(12) United States Patent
van Eis et al.

(10) Patent No.: US 8,193,236 B2
(45) Date of Patent: Jun. 5, 2012

(54) INDOLYLMALEIMIDE DERIVATIVES PROCESSES FOR THEIR PRODUCTION AND PHARMACEUTICAL COMPOSITIONS

(75) Inventors: Maurice van Eis, St. Louis (FR); Peter von Matt, Biel-Benken (CH); Jurgen Wagner, Bottmingen (CH)

(73) Assignee: Novartis AG, Basel (CH)

( * ) Notice: Subject to any disclaimer, the term of this patent is extended or adjusted under 35 U.S.C. 154(b) by 222 days.

(21) Appl. No.: 12/520,025

(22) PCT Filed: Dec. 14, 2007

(86) PCT No.: PCT/EP2007/064010
§ 371 (c)(1),
(2), (4) Date: Jun. 18, 2009

(87) PCT Pub. No.: WO2008/074752
PCT Pub. Date: Jun. 26, 2008

(65) Prior Publication Data
US 2010/0041693 A1      Feb. 18, 2010

(30) Foreign Application Priority Data

Dec. 19, 2006   (EP) ..................................... 06126534

(51) Int. Cl.
*A61K 31/405*   (2006.01)
(52) U.S. Cl. .......................... 514/415; 548/469; 548/565
(58) Field of Classification Search .................. 514/415; 548/469, 565
See application file for complete search history.

(56) References Cited

U.S. PATENT DOCUMENTS

| | | | |
|---|---|---|---|
| 5,821,072 A | 10/1998 | Schwartz et al. | |
| 6,228,877 B1 * | 5/2001 | Dhingra et al. | 514/414 |
| 2003/0078280 A1 | 4/2003 | Kuo et al. | |

FOREIGN PATENT DOCUMENTS

| | | |
|---|---|---|
| WO | 95/35294 A | 12/1995 |
| WO | 02/38561 A1 | 5/2002 |
| WO | 03/076398 A | 9/2003 |
| WO | 03/082859 A | 10/2003 |
| WO | 03/103663 A | 12/2003 |
| WO | 2004/072062 A | 8/2004 |
| WO | 2005/000836 A | 1/2005 |
| WO | 2006/086484 A1 | 8/2006 |
| WO | 2007/006533 A2 | 1/2007 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, New York: John Wiley & Sons, 1996, 1, 975-976.*
Australian Examination, Application No. 2007336338, Aug. 31, 2010, 2 pgs.
Bit et al., "Inhibitors of Protein Kinase C. 3. Potent and Highly Selective Bisindolylmaleimides by Conformational Restriction", Journal of Medicinal Chemistry, American Chemical Society, vol. 36, No. 1 (1993), pp. 21-29.
Davis et al., "Inhibitors of Protein Kinase C. $1.^1$ 2,3-Bisarylmaleimides", Journal of Medicinal Chemistry, American Chemical Society, vol. 35, No. 1 (1992), pp. 177-184.
Engler et al., "The development of potent and selective bisarylmaleimide GSK3 inhibitors", Bioorganic & Medicinal Chemistry Letters, vol. 15, No. 4 (2005), pp. 899-903.

* cited by examiner

*Primary Examiner* — James O Wilson
*Assistant Examiner* — Douglas M Willis
(74) *Attorney, Agent, or Firm* — Paul D. Strain, Esq.; Strain & Strain PLLC

(57) ABSTRACT

A compound of formula (I)

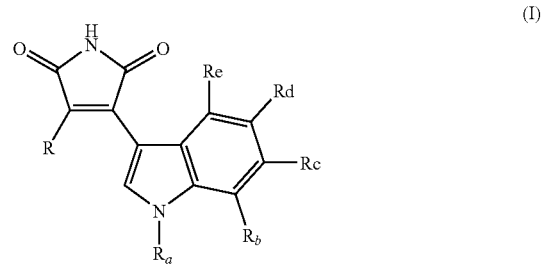

(I)

wherein R denotes another heterocylic residue and wherein $R_a$, $R_b$, $R_c$, $R_d$ and $R_e$, are as defined in the specification, processes for their production, their uses, in particular in transplantation, and pharmaceutical compositions containing them.

7 Claims, No Drawings

INDOLYLMALEIMIDE DERIVATIVES PROCESSES FOR THEIR PRODUCTION AND PHARMACEUTICAL COMPOSITIONS

CROSS-REFERENCE TO RELATED APPLICATIONS

This application is the US National Stage of Application No. PCT/EP2007/064010, filed Dec. 14, 2007 which claims benefit under 35 U.S.C. §119(a)-(d) or (f) or 365(b) of EP Application No. 06126534.4, filed Dec. 19, 2006, the contents of which are incorporated herein by reference in their entirety.

BACKGROUND OF THE INVENTION

The present invention relates to new indolylmaleimide derivatives, processes for their production and pharmaceutical compositions containing them.

DESCRIPTION OF THE INVENTION

More particularly the present invention provides a compound of formula (I)

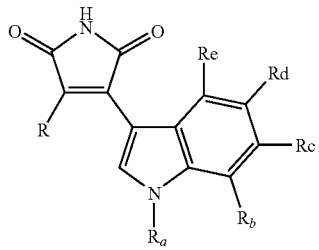

(I)

wherein $R_a$ is hydrogen or optionally substituted $C_{1-6}$alkyl;

$R_b$ is hydrogen; halogen; CN; $C_{1-6}$alkyl optionally substituted e.g. by OH, $C_{1-6}$alkoxy, $NH_2$, $NHC_{1-6}$alkyl, or $N(C_{1-6}alkyl)_2$; halo$C_{1-6}$alkyl; optionally substituted $C_{1-6}$alkoxy; or optionally substituted $C_{1-6}$alkoxy-chain;

$R_c$ is hydrogen; halogen; CN; optionally substituted $C_{1-6}$alkyl; optionally substituted $C_{1-6}$alkoxy;

each of $R_d$ and $R_e$ independently, is hydrogen; halogen; CN; optionally substituted $C_{1-6}$alkyl;

and R is a radical of formula (a), (b), (c), (d), (e) or (f);

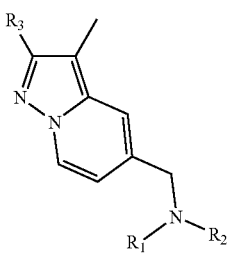

(a)

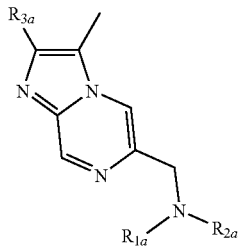

(b)

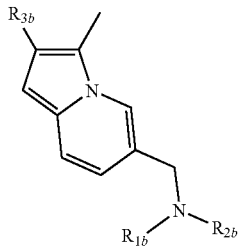

(c)

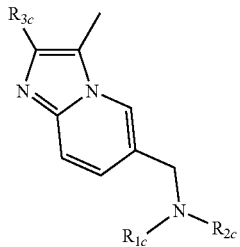

(d)

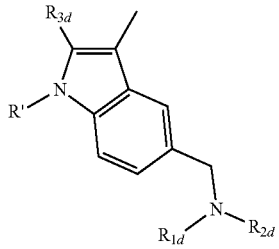

(e)

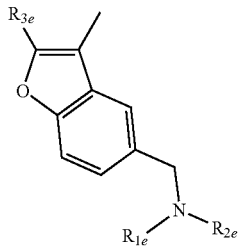

(f)

wherein either each of $R_1$, $R_{1a}$, $R_{1b}$, $R_{1c}$, $R_{1d}$, $R_{1e}$, $R_2$, $R_{2a}$, $R_{2b}$, $R_{2c}$, $R_{2d}$, and $R_{2e}$ independently, is hydrogen; $C_{1-6}$alkyl optionally interrupted by an oxygen atom and/or optionally substituted by OH, $C_{1-6}$alkoxy, $NH_2$, $NHC_{1-4}$alkyl, $N(C_{1-4}alkyl)_2$, $C_{3-8}$cycloalkyl or heterocylic residue; $C_{3-8}$cycloalkyl; or halo$C_{1-6}$alkyl;

or $R_1$ and $R_2$, $R_{1a}$ and $R_{2a}$, $R_{1b}$ and $R_{2b}$, $R_{1c}$ and $R_{2c}$, $R_{1d}$ and $R_{2d}$, or $R_{1e}$ and $R_{2e}$, respectively, form together with the nitrogen atom to which they are bound a heterocyclic residue;

each of $R_3$, $R_{3a}$, $R_{3b}$, $R_{3c}$, $R_{3d}$, and $R_{3e}$, independently, is hydrogen; halogen; CN; $NO_2$; $C_{1-6}$alkyl; halo$C_{1-6}$alkyl;

R' is hydrogen; $C_{1-6}$alkyl; halo-$C_{1-6}$alkyl; $CH_2$—$C_{1-5}$ alkyl, the $C_{1-5}$alkyl being optionally substituted by OH, $C_{1-6}$alkoxy, $NH_2$, $NHC_{1-6}$alkyl, or $N(C_{1-6}$alkyl$)_2$;

or a physiologically hydrolysable derivative thereof, a salt, hydrate and/or solvate thereof.

Halogen may be F, Cl, Br or I, preferably F, Cl or Br, even more preferably F.

Alkyl or alkoxy, as a group or present in a group, may be straight or branched.

Possible substitutents of alkyl or alkoxy (as such or present in an alkoxy-chain) include, but are not limited to, e.g. OH, halogen, $NH_2$, $NHC_{1-6}$alkyl, $N(C_{1-6}$alkyl$)_2$, $C_{1-6}$alkoxy, $C_{3-8}$cycloalkyl and heterocyclic residue.

When an alkyl or alkoxy is substituted, e.g. by OH, $NH_2$, $NHC_{1-3}$alkyl, $N(C_{1-3}$alkyl$)_2$, $C_{3-8}$cycloalkyl or an heterocyclic residue, the substituent is preferably at the terminal position of the alkyl or alkoxy chain.

By halo$C_{1-6}$alkyl, e.g. as $R_b$, $R_1$, $R_2$, $R_{1a}$, $R_{2a}$, $R_{1b}$, $R_{2b}$, $R_{1d}$, $R_{2d}$, $R_3$, or R', or halo$C_{1-6}$alkoxy, is meant $C_{1-6}$alkyl or $C_{1-6}$alkoxy, substituted by 1 to 5 halogen, e.g. —$CH_2F$, —$CHF_2$, —$CF_3$, —$CHF_2$—$CH_2$—O— or —$CF_3$—$CH_2$—O—, preferably —$CF_3$.

By $C_{1-6}$alkyl interrupted by an oxygen atom, e.g. as $R_1$, $R_{1a}$, $R_{1b}$, $R_{1c}$, $R_{1d}$, $R_{1e}$, $R_2$, $R_{2a}$, $R_{2b}$, $R_{2c}$, $R_{2d}$, or $R_{2e}$, is meant $C_a$alkyl-O—$C_b$alkyl, wherein the sum of "a" plus "b" is comprised between 1 and 6, and a being different from 0. Said indices a and b are selected from an integer.

By alkoxy is meant —O-alkyl. Preferably the alkoxy is —O—$CH_3$.

By alkoxy-chain is meant —O-alkyl wherein the alkyl is optionally interrupted by one or two O atoms. Examples of alkoxy-chain include, but is not limited to $OCH_2CH_2OCH_2CH_2OCH_3$, or $OCH_2CH_2OCH_3$. Preferably the alkoxy-chain is terminated by —O—$CH_3$.

Alkoxy and alkoxy-chain, e.g. as $R_b$, may be unsubstituted or substituted e.g. by halogen, OH, $NH_2$, $NHC_{1-6}$alkyl, or $N(C_{1-6}$alkyl$)_2$.

By $C_{3-8}$cycloalkyl, e.g. as $R_1$, $R_{1a}$, $R_{1b}$, $R_{1c}$, $R_{1d}$, $R_{1e}$, $R_2$, $R_{2a}$, $R_{2b}$, $R_{2c}$, $R_{2d}$, or $R_{2e}$ is meant a three to eight, preferably five to seven, membered non aromatic ring.

By heterocyclic residue, e.g. as a substituent of alkyl or formed by $R_1$ and $R_2$, $R_{1a}$ and $R_{2a}$, $R_{1b}$ and $R_{2b}$, $R_{1c}$ and $R_{2c}$, $R_{1d}$ and $R_{2d}$, or $R_{1e}$ and $R_{2e}$, together with N to which they are bound, respectively, is meant a five to eight, preferably five to six, membered saturated heterocyclic ring comprising 1 or 2 heteroatoms, preferably selected from N and O. In case the heterocyclic residue is a substituent of an alkyl chain, then the alkyl chain comprises at least 2 carbon atoms and the heterocyclic residue is not linked to the first carbon atom of the alkyl chain. In case the heterocyclic residue is a substituent of an alkyl chain, it may be linked to the alkyl chain through either a/the ring heteroatom, e.g. N, or through a ring carbon atom. According to the invention, the heterocyclic residue is optionally substituted, on one or more ring carbon atoms and/or, e.g. in the case of the heterocyclic residue formed by $R_1$ and $R_2$, $R_{1a}$ and $R_{2a}$, $R_{1b}$ and $R_{2b}$, $R_{1c}$ and $R_{2c}$, $R_{1d}$ and $R_{2d}$, or $R_{1e}$ and $R_{2e}$ and the N atom to which they are attached, on a ring heteroatom when present.

Examples of heterocyclic residues may be derived from a piperidine, pyrrolidine, morpholine, or a piperazine.

Examples of a substituent on a ring carbon atom include e.g. $C_{1-6}$alkyl, e.g. $CH_3$. The preferred heterocyclic residue is piperazinyl, optionally substituted, e.g. by a $C_{1-6}$alkyl residue, e.g. on the heteroatom.

According to the invention, the following significances are preferred individually or in any sub-combination:

1. $R_a$ is hydrogen or $C_{1-6}$alkyl, e.g. $CH_3$;
2. $R_b$ is hydrogen; $C_{1-6}$alkyl (e.g. $CH_3$); halo-$C_{1-6}$alkyl; $C_{1-6}$alkoxy unsubstituted or substituted by halogen; $C_{1-6}$alkoxy-chain unsubstituted or substituted by halogen;
3. $R_c$ is hydrogen or $C_{1-6}$alkyl;
4. $R_d$ is hydrogen or $C_{1-6}$alkyl;
5. $R_e$ is hydrogen;
6. R is a radical of formula (a);
7. R is a radical of formula (d);
8. R is a radical of formula (e);
9. R is a radical selected from formula (a), (b), (c), (d), and (f);
10. each of $R_1$ and $R_2$, independently, is hydrogen; $C_{1-6}$alkyl optionally interrupted by one O oxygen (e.g. $CH_2CH_2OCH_3$) and optionally substituted by $C_{1-6}$alkoxy; or halo$C_{1-6}$alkyl (e.g. $CH_2F$);
11. each of $R_{1a}$ and $R_{2a}$, independently, is hydrogen, or $C_{1-6}$alkyl or halo$C_{1-6}$alkyl (e.g. $CF_3$);
12. each of $R_{1c}$ and $R_{2c}$ is hydrogen;
13. each of $R_{1d}$ and $R_{2d}$, independently, is hydrogen, $C_{1-6}$alkyl (optionally substituted by $C_{1-6}$alkoxy or $C_{3-8}$cycloalkyl), halo$C_{1-6}$alkyl, or $C_{3-8}$cycloalkyl;
14. each of $R_{1e}$ and $R_{2e}$, independently, is hydrogen or $C_{1-6}$alkyl optionally substituted by $C_{3-8}$cycloalkyl;
15. $R_1$ and $R_2$ form together with the nitrogen atom to which they are bound a heterocyclic residue, e.g. a piperazinyl;
16. $R_3$ is hydrogen, $C_{1-6}$alkyl, or halo$C_{1-6}$alkyl (e.g. $CF_3$);
17. R' is hydrogen, halo-$C_{1-6}$alkyl (e.g. $CF_3$) or $C_{1-6}$alkyl;
18. R is a radical of formula (a); $R_a$ is hydrogen or $C_{1-6}$alkyl; $R_b$ is hydrogen, $C_{1-6}$alkyl, $C_{1-6}$alkoxy optionally substituted by halogen or $C_{1-6}$alkoxy-chain optionally substituted by halogen; each of $R_c$, $R_d$ and $R_e$ is hydrogen; each of $R_1$ and $R_2$, independently, is hydrogen, $C_{1-6}$alkyl optionally interrupted by one O atom, or halo$C_{1-6}$alkyl; $R_3$ is hydrogen or $C_{1-6}$alkyl;
19. R is a radical of formula (b); each of $R_a$ and $R_b$, independently, is hydrogen or $C_{1-6}$alkyl; each of $R_c$, $R_d$ and $R_e$ is hydrogen; each of $R_1$, $R_2$, and $R_3$, independently, is hydrogen or $C_{1-6}$alkyl;
20. R is a radical of formula (c); each of $R_a$, $R_c$, $R_d$ and $R_e$ is hydrogen; $R_b$ is hydrogen or $C_{1-6}$alkyl; each of $R_1$, $R_2$, and $R_3$, independently, is hydrogen or $C_{1-6}$alkyl;
21. R is a radical of formula (d); each of $R_a$ and $R_b$, independently, is hydrogen or $C_{1-6}$alkyl; each of $R_c$, $R_d$ and $R_e$ is hydrogen; each of $R_1$, $R_2$, and $R_3$, independently, is hydrogen or $C_{1-6}$alkyl;
22. R is a radical of formula (e); each of $R_a$, $R_b$, and $R_c$, independently, is hydrogen or $C_{1-6}$alkyl; each of $R_d$ and $R_e$ is hydrogen; each of $R_1$ and $R_2$, independently, is hydrogen, $C_{1-6}$alkyl (optionally substituted by cyclo$C_{3-8}$alkyl), cyclo$C_{3-8}$alkyl or halo$C_{1-6}$alkyl (e.g. $CH_2H_2F$); $R_3$ is hydrogen, $C_{1-6}$alkyl, or halo$C_{1-6}$alkyl (e.g. $CF_3$); R' is hydrogen, or $C_{1-6}$alkyl optionally substituted OH;
23. R is a radical of formula (f); each of $R_a$, $R_b$, and $R_c$, independently, is hydrogen or $C_{1-6}$alkyl; each of $R_d$ and $R_e$ is hydrogen; each of $R_1$ and $R_2$, independently, is hydrogen, $C_{1-6}$alkyl or cyclo$C_{3-8}$alkyl; $R_3$ is hydrogen or $C_{1-6}$alkyl.

The present invention also includes a process for the preparation of a compound of formula (I), which process comprises reacting a compound of formula (I')

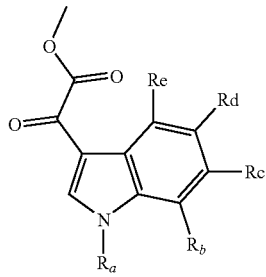
(I')

wherein the variables are as defined hereinabove, with a compound of formula (I")

R—CH$_2$—CO—NH$_2$ (I");

wherein R is a residue of formula (I''')

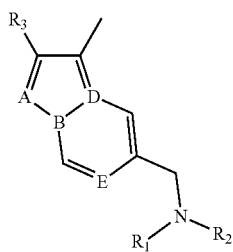
(I''')

wherein
R$_1$, R$_2$, and R$_3$ are as described hereinabove,
either A and B are Nitrogen atoms and D and E are Carbon atoms;
or A and D are Nitrogen atoms, B is Carbon atom and either E is Carbon atom or Nitrogen atom;
or A, B and E are all Carbon atoms and D is Nitrogen atom;
or A is either Nitrogen atom optionally substituted by C$_{1-6}$alkyl or by hydroxyl-C$_{1-6}$alkyl or Oxygen atom and B, D and E are all Carbon atoms;
or A is Nitrogen atom optionally substituted by C$_{1-6}$alkyl or hydroxyl-C$_{1-6}$alkyl and B, D and E are all Carbon atoms
and, where required, converting the resulting compound of formula (I) obtained in free form to a salt form or vice versa, as appropriate. In a compound of formula (I'), the methyl-ester group may be typically replaceable by a C$_2$- to C$_8$-alkyl-ester group or a benzyl-ester group.

The processes may conveniently be effected in the presence of a strong base, e.g. t-BuOK, e.g. as disclosed in WO02/38561, WO2005/068454 and WO2005/068455, the contents of which being incorporated herein by reference, and as illustrated in the Examples.

Compounds of formula (I') may be prepared in accordance with known methods, e.g. as disclosed in WO02/38561, WO 03/08259, WO2005/068454, WO2005/068455 and PCT/EP2006/006732, the contents of which being incorporated herein by reference, and as illustrated in the Examples.

The following examples are illustrative of the invention without any limitation.
AIBN=azobisisobutyronitrile
DBU=1,8-diazabicyclo[5.4.0]undec-7-ene
DMF=dimethylformamide
EtOAc=ethylacetate
FCC=flash column chromatography
RT=room temperature
THF=tetrahydrofuran
TLC=thin layer chromatography

EXAMPLE 1

3-(5-Dimethylaminomethyl-2-methyl-pyrazolo[1,5-a]pyridin-3-yl)-4-(7-methyl-1H-indol-3-yl)-pyrrole-2,5-dione

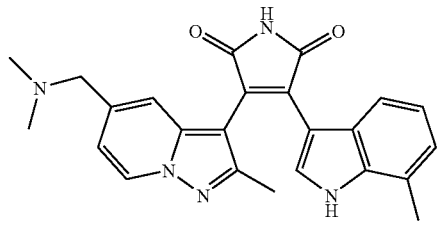

Dimethylamine (approx. 50% solution in DMF, 0.04 ml, 0.27 mmol, 2.0 equiv) is added at room temperature under an atmosphere of argon to a solution of methanesulfonic acid 2-methyl-3-[4-(7-methyl-1H-indol-3-yl)-2,5-dioxo-2,5-dihydro-1H-pyrrol-3-yl]-pyrazolo[1,5-a]pyridin-5-ylmethyl ester (80 mg, 0.17 mmol). The reaction mixture is stirred at room temperature for 20 minutes. After dilution with water, the mixture is extracted three times with EtOAc. The combined organic layers are washed with brine, dried over Na$_2$SO$_4$, filtered and concentrated in vacuo. Purification via flash chromatography (CH$_2$Cl$_2$/MeOH 95:5) affords the title compound (44 mg, 62%). $^1$H NMR (400 MHz, d$_6$-DMSO): δ=11.77 (s, 1H), 10.93 (s, 1H), 8.48 (d, J=6.9Hz, 1H), 7.94 (d, J=3.0 Hz, 1H), 6.79 (br s, 1H), 6.74 (d=7.1 Hz, 1H), 6.65 (dd, J=7.1/1.7 Hz, 1H), 6.45 (t, J=7.1 Hz, 1H), 6.11 (d, J=8.1 Hz, 1H), 4.10 (q, J=5.4 Hz, 2H), 3.18 (s, 3H), 3.17 (s, 3H), 2.39 (s, 3H), 2.20 (s, 3H). MS (ES$^+$): 414 (M+H)$^+$.

Methanesulfonic acid 2-methyl-3-[4-(7-methyl-1H-indol-3-yl)-2,5-dioxo-2,5-dihydro-1H-pyrrol-3-yl]-pyrazolo[1,5-a]pyridin-5-ylmethyl ester

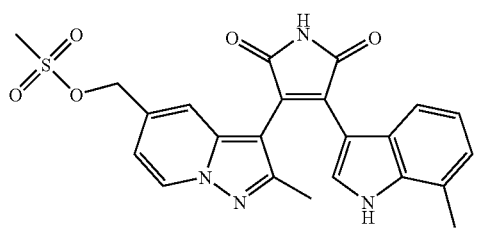

Methanesulfonic anhydride (815 mg, 4.49 mmol, 4.3 equiv) is added at room temperature under an atmosphere of argon to a solution of 3-(5-hydroxymethyl-2-methyl-pyrazolo[1,5-a]pyridin-3-yl)-4-(7-methyl-1H-indol-3-yl)-pyrrole-2,5-dione (400 mg, 1.04 mmol) and of triethyl amine (0.314 ml, 2.25 mmol, 2.2 equiv) in anhydrous THF (10 ml).

The reaction mixture is stirred for 1 hour at room temperature. Water is added, and the mixture is extracted three times with EtOAc. The combined organic layers are dried over Na$_2$SO$_4$, filtered, and concentrated in vacuo. The residue (450 mg, 94%) is used directly in the next transformation.

3-(5-Hydroxymethyl-2-methyl-pyrazolo[1,5-a]pyridin-3-yl)-4-(7-methyl-1H-indol-3-yl)-pyrrole-2,5-dione

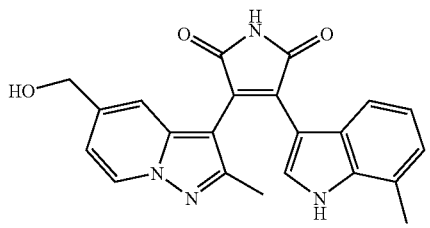

TBAF (1.0 M in THF, 1.4 ml, 1.4 mmol, 1.1 equiv) is added to a solution of 3-[5-(tert-Butyl-diphenyl-silanyloxymethyl)-2-methyl-pyrazolo[1,5-a]pyridin-3-yl]-4-(7-methyl-1H-indol-3-yl)-pyrrole-2,5-dione in THF (10 ml). The reaction mixture is stirred for 1 hour at room temperature. The solvent is removed in vacuo, and the residue is purified by flash chromatography (gradient of hexane/EtOAc 100:0 to 20:80) to afford the title compound (400 mg, 84%). $^1$H NMR (400 MHz, d$_6$-DMSO): δ=11.85 (br s, 1H), 10.99 (br s, 1H), 8.53 (d, J=7.8 Hz, 1H), 7.94 (d, J=2.7 Hz, 1H), 7.35-7.34 (m, 1H), 6.82-6.79 (m, 2 H), 6.51 (t, J=8.1 Hz, 1H), 6.22 (d, J=8.1 Hz, 1H), 5.38 (t, J=5.7 Hz, 1H), 4.45 (d, J=4.9 Hz, 2H), 2.45 (s, 3H), 1.79 (s, 3H). MS (ES$^+$): 387 (M+H)$^+$.

3-[5-(tert-Butyl-diphenyl-silanyloxymethyl)-2-methyl-pyrazolo[1,5-a]pyridin-3-yl]-4-(7-methyl-1H-indol-3-yl)-pyrrole-2,5-dione

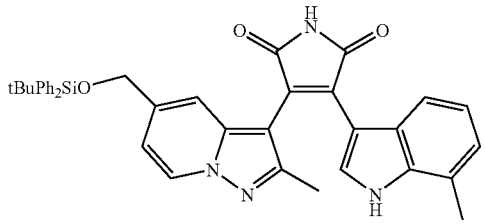

Potassium tert-butoxide (1.0 M in THF, 6.4 ml, 6.4 mmol, 3.0 equiv) is added dropwise at room temperature under an atmosphere of argon to a solution of 2-(7-methyl-1H-indol-3-yl)-acetamide (400 mg, 2.13 mmol, 1.0 equiv) and of [5-(tert-butyl-diphenyl-silanyloxymethyl)-2-methyl-pyrazolo[1,5-a]pyridin-3-yl]-oxo-acetic acid methyl ester (1.04 g, 2.13 mmol, 1.0 equiv) in anhydrous tetrahydrofuran (10 ml, dried over molecular sieves). The reaction mixture is stirred for 15 minutes at room temperature. It is then diluted with EtOAc and poured into a saturated aqueous NH$_4$Cl solution. After three extractions with EtOAc, the combined organic layers are dried over Na$_2$SO$_4$, filtered and concentrated in vacuo. The residue is dissolved in N,N-dimethylformamide (20 ml), treated with DBU (3.2 ml, 21.3 mmol, 10 equiv) and stirred under an atmosphere of argon for 10 minutes at 100° C. After cooling, the reaction mixture is diluted with water and extracted three times with EtOAc. The combined organic layers are washed with brine, dried over Na$_2$SO$_4$, filtered and concentrated in vacuo. Purification of the residue via flash chromatography (gradient of hexane/EtOAc 100:0 to 50:50) affords the title compound (750 mg, 56%). $^1$H NMR (400 MHz, d$_6$-DMSO): δ=11.83 (br s, 1H), 11.02 (br s, 1H), 8.54 (d, J=7.8 Hz, 1H), 7.93 (d, J=3.0 Hz, 1H), 7.61-7.59 (m, 4H), 7.48-7.39 (m, 6H), 7.34 (s, 1H), 6.82 (d, J=7.1 Hz, 1H), 6.74 (dd, J=7.1/1.7 Hz, 1H), 6.52 (t, J=7.1 Hz, 1H), 6.20 (d, J=8.1 Hz, 1H), 4.69 (s, 2H), 2.44 (s, 3H), 1.91 (s, 3H), 1.01 (s, 9H). MS (ES$^+$): 625 (M+H)$^+$.

[5-(tert-Butyl-diphenyl-silanyloxymethyl)-2-methyl-pyrazolo[1,5-a]pyridin-3-yl]-oxo-acetic acid methyl ester

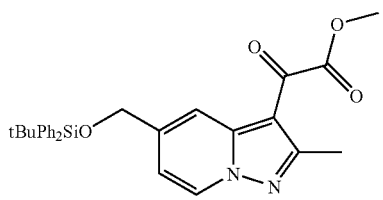

In a reaction tube, chloro-oxo-acetic acid methyl ester (2.47 ml, 26.0 mmol, 4.0 equiv) is added to a solution of 5-(tert-butyl-diphenyl-silanyloxymethyl)-2-methyl-pyrazolo[1,5-a]pyridine (2.6 g, 6.49 mmol) in THF (20 ml) under an atmosphere of argon. The tube is sealed under argon, and the reaction mixture is heated under microwave irradiation for 15 minutes at 120° C. After cooling, the reaction mixture is carefully poured into an aqueous solution of sodium carbonate. After three extractions with EtOAc, the combined organic layers are dried over Na$_2$SO$_4$, filtered and concentrated in vacuo. Purification via flash chromatography (hexane/EtOAc 4:1) affords the title compound (2.9 g, 92%). $^1$H NMR (400 MHz, d$_6$-DMSO): δ=8.76 (d, J=7.8 Hz, 1H), 8.11 (br s, 1H), 7.61-7.59 (m, 4H), 7.44-7.35 (m, 6H), 7.10 (dd, J=7.1/1.9 Hz, 1H), 4.88 (s, 2H), 3.82 (s, 3H), 2.41 (s, 3H), 1.03 (s, 9H). MS (ES$^+$): 487 (M+H)$^+$.

5-(tert-Butyl-diphenyl-silanyloxymethyl)-2-methyl-pyrazolo[1,5-a]pyridine

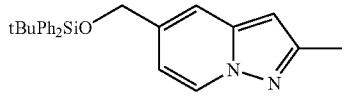

A solution of O-mesitylenesulfonylhydroxylamine (18.6 g, 77.8 mmol, 5.0 equiv) in chloroform (50 ml) is added at 0-10° C. to a solution of 4-(tert-butyl-diphenyl-silanyloxymethyl)-2-prop-1-ynyl-pyridine in chloroform (50 ml). The resulting mixture is stirred at room temperature overnight. The solvent is removed in vacuo, and N,N-dimethylformamide (50 ml) is added to the residue. Potassium carbonate (4.30 g, 31.1 mmol, 2.0 equiv) is added, and the mixture is stirred at room temperature for 2 hours. The reaction mixture is diluted with water and extracted three times with EtOAc. The combined organic layers are washed with brine, dried over Na$_2$SO$_4$, filtered and concentrated in vacuo. Purification via flash chromatography (gradient from hexane/EtOAc 100:0 to 30:70) affords the title compound (2.6 g, 42%). ¹H NMR (400 MHz, d₆-DMSO): δ=8.42 (d, J=7.1 Hz, 1H), 7.60-7.58 (m, 4H), 7.43-7.35 (m, 7H), 6.64 (dd, J=7.3/1.9 Hz, 1H), 6.27 (s, 1H), 4.71 (s, 2H), 2.30 (s, 3H), 0.99 (s, 9H). MS (ES⁺): 401 (M+H)⁺.

4-(tert-Butyl-diphenyl-silanyloxymethyl)-2-prop-1-ynyl-pyridine

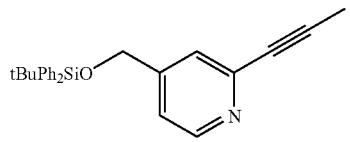

A reaction tube is charged under an atmosphere of argon with 4-(tert-butyl-diphenyl-silanyloxymethyl)-2-chloro-pyridine (9.47 g, 24.79 mmol), palladium(II)-bis(triphenylphosphine)-dichloride (1.78 g, 2.49 mmol, 0.1 equiv), copper(I) iodide (477 mg, 2.49 mmol, 0.1 equiv), and triphenylphosphine (3.94 g, 14.9 mmol, 0.6 equiv). The tube is degassed by alternating three times between vacuum and argon. Diethylamine (39 ml) and N,N-dimethylformamide (2.0 ml), and propyne (50% in THF, 10.1 g, 247 mmol, 10 equiv) are added under an argon atmosphere. The tube is sealed, and the reaction mixture is heated under microwave irradiation for 20 minutes at 120° C. After cooling, the reaction mixture is poured into a semi-concentrated aqueous solution of NaHCO₃. After three extractions with EtOAc, the combined organic layers are washed with brine, dried over Na₂SO₄, filtered and concentrated in vacuo. Purification via flash chromatography (gradient from hexane/EtOAc 100:0 to 50:50) affords the title compound (6.0 g, 63%). ¹H NMR (400 MHz, d₆-DMSO): δ=8.41 (d, J=5.0 Hz, 1H), 7.57-7.55 (m, 4H), 7.43-7.32 (m, 11H), 7.27 (d, J=5.0 Hz, 1H), 4.72 (s, 2H), 1.99 (s, 3H), 0.98 (s, 9H). MS (ES⁺): 386 (M+H)⁺.

4-(tert-Butyl-diphenyl-silanyloxymethyl)-2-chloropyridine

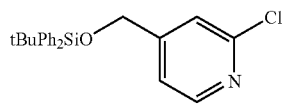

Imidazole (2.32 g, 33.7 mmol, 1.1 equiv) and tert-butyl-diphenylsilylchloride (8.0 ml, 33.7 mmol, 1.1 equiv) are added sequentially at room temperature to a solution of (2-chloro-pyridin-4-yl)-methanol (4.4 g, 30.6 mmol) in N,N-dimethylformamide (20 ml). The reaction mixture is stirred at room temperature for 1 hour. TLC analysis indicated complete consumption of starting material. The solvent is removed in vacuo, and the residue is purified via flash chromatography (hexane/EtOAc 90:10) to yield the title compound (10.7 g, 91%). ¹H NMR (400 MHz, CDCl₃): δ=8.35 (d, J=5.0 Hz, 1H), 7.69-7.67 (m, 4H), 7.48-7.35 (m, 11H), 7.20 (d, J=5.0 Hz, 1H), 4.75 (s, 2H), 1.14 (s, 9H). MS (ES⁺): 383 (M+H)⁺.

(2-Chloro-pyridin-4-yl)-methanol

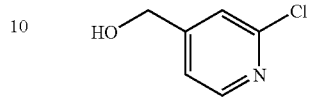

Carbonyldiimidazole (CDI, 7.88 g, 46.2 mmol, 1.5 equiv) is added at room temperature to a solution of 2-chloroisonicotinic acid (5.0 g, 30.8 mmol) in THF (70 ml). The reaction mixture is stirred at rt overnight, and then added dropwise to a cold (0° C.) solution of NaBH₄ (6.07 g, 154 mmol, 5.0 eq) in water (175 ml). After stirring for 10 minutes at 0° C., HCl (2 M aqueous solution) is carefully added. Volatiles are removed via rotary evaporation, and the residue is dissolved in an aqueous 10% solution of NaHCO₃. After five extractions with EtOAc, the combined organic layers are dried over Na₂SO₄, filtered and concentrated in vacuo. ¹H-NMR analysis of the residue indicated adequate purity for direct use of the product (4.40 g, 99%) in the next step. ¹H NMR (400 MHz, CDCl₃): δ=8.37 (d, J=5.1 Hz, 1H), 7.39 (s, 1H), 7.23 (d, J=5.1 Hz, 1H), 4.78 (s, 2H). MS (ES⁺): 144 (M+H)⁺.

By following the procedures of Example 1, the compounds of formula A wherein $R_a$, $R_b$, $R_1$ and $R_2$ are as indicated in Table 1 below, may be obtained.

TABLE 1

A

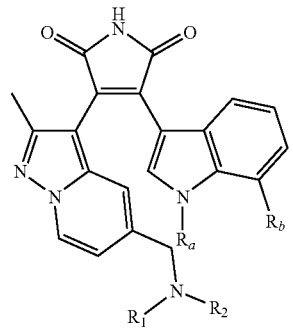

| | $R_1$ | $R_2$ | $R_a$ | $R_b$ | MS |
|---|---|---|---|---|---|
| 2. | H | CH₃ | H | H | MH⁺ 386 |
| 3. | H | CH₂CH₂OCH₃ | H | H | MH⁺ 431 |
| 4. | H | CH₂CH₂F | H | H | MH⁺ 419 |
| 5. | H | CH₃ | H | CH₃ | MH⁺ 401 |
| 6. | CH₃ | CH₃ | H | CH₃ | MH⁺ 415 |
| 7. | H | CH₂CH₂OCH₃ | H | CH₃ | MH⁺ 445 |
| 8. | H | CH₂CH₂F | H | CH₃ | MH⁺ 433 |
| 9. | CH₃ | CH₃ | CH₃ | H | MH⁺ 415 |
| 10. | H | CH₃ | CH₃ | H | MH⁺ 401 |
| 11. | H | CH₂CH₂OCH₃ | CH₃ | H | MH⁺ 445 |
| 12. | CH₃ | CH₃ | H | OCH₂CH₂OCH₂CH₂OCH₃ | MH⁺ 519 |
| 13. | CH₃ | CH₃ | H | OCH₂CH₂OCH₃ | MH⁺ 475 |
| 14. | H | CH₃ | H | OCH₂CH₂OCH₃ | MH⁺ 461 |
| 15. | CH₃ | CH₃ | H | OCH₃ | MH⁺ 431 |
| 16. | H | CH₃ | H | OCH₃ | MH⁺ 417 |
| 17. | H | CH₃ | H | OCH₂CH₂OCH₂CH₂OCH₃ | MH⁺ 505 |

TABLE 1-continued

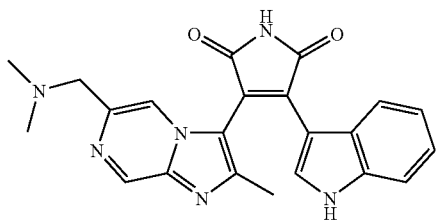

A

| | $R_1$ | $R_2$ | $R_a$ | $R_b$ | MS |
|---|---|---|---|---|---|
| 18. | CH$_3$ | CH$_3$ | H | OCH$_2$CH$_2$F | MH$^+$ 463 |
| 19. | H | CH$_3$ | H | OCH$_2$CH$_2$F | MH$^+$ 449 |

EXAMPLE 20

3-(6-Dimethylaminomethyl-2-methyl-imidazo[1,2-a]pyrazin-3-yl)-4-(1H-indol-3-yl)-pyrrole-2,5-dione

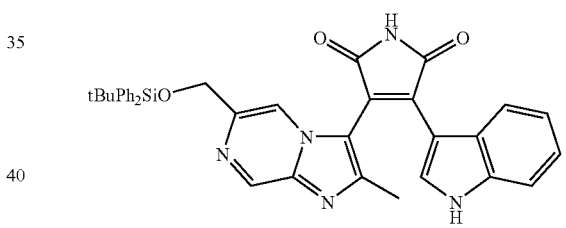

Methanesulfonic anhydride (30 mg, 0.20 mmol, 4.0 equiv) is added at room temperature under an atmosphere of argon to a solution of 3-(6-hydroxymethyl-2-methyl-imidazo[1,2-a]pyrazin-3-yl)-4-(1H-indol-3-yl)-pyrrole-2,5-dione (20 mg, 0.05 mmol) and of triethylamine (0.014 ml, 0.10 mmol, 2.0 equiv) in anhydrous THF (5.0 ml). The reaction mixture is stirred for 1 hour at room temperature. Volatiles are removed in vacuo, and the residue is dissolved in a solution of dimethylamine in EtOH (33%, 5.0 ml). The reaction mixture is stirred at room temperature for 10 minutes. After addition of water, the mixture is extracted three times with EtOAc. The combined organic layers are washed with brine, dried over Na$_2$SO$_4$, filtered, and concentrated in vacuo. Purification by preparative HPLC yields the title compound as its trifluoroacetate salt (11 mg, 54%). $^1$H NMR (400 MHz, d$_6$-DMSO): δ=11.32 (s, 1H), 10.56 (s, 1H), 9.06 (s, 1H), 8.29 (s, 1H), 7.97 (s, 1H), 7.41 (d, J=7.4 Hz, 1H), 7.03 (t, J=8.1 Hz, 1H), 6.54 (t, J=8.1 Hz, 1H), 5.73 (d, J=8.0 Hz, 1H), 4.23-4.19 (m, 2H), 2.61 (s, 3H). MS (ES$^+$): 401 (M+H)$^+$.

3-(6-Hydroxymethyl-2-methyl-imidazo[1,2-a]pyrazin-3-yl)-4-(1H-indol-3-yl)-pyrrole-2,5-dione

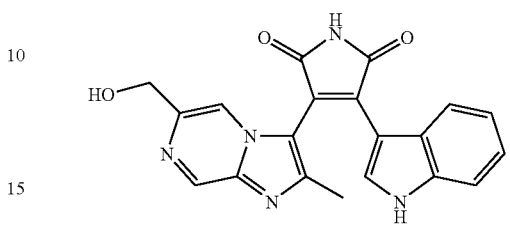

Hydrochloric acid (1.0 ml of a 4.0 M solution in dioxane) is added to 3-[6-(tert-butyl-diphenyl-silanyloxymethyl)-2-methyl-imidazo[1,2-a]pyrazin-3-yl]-4-(1H-indol-3-yl)-pyrrole-2,5-dione (60 mg, 0.098 mmol). The reaction mixture is heated to 50° C. for 16 hours under an atmosphere of argon. After cooling, volatiles are removed in vacuo, and the residue is purified by flash chromatography (gradient of CH$_2$Cl$_2$/MeOH 100:0 to 90:10) to afford the title compound (25 mg, 68%). MS (ES$^+$): 374 (M+H)$^+$.

3-[6-(tert-Butyl-diphenyl-silanyloxymethyl)-2-methyl-imidazo[1,2-a]pyrazin-3-yl]-4-(1H-indol-3-yl)-pyrrole-2,5-dione Potassium tert-butoxide (1.0 M in THF, 0.86 ml, 0.86 mmol, 3.0 equiv) is added dropwise at room temperature under an atmosphere of argon to a solution of 2-(1H-indol-3-yl)-acetamide (50 mg, 0.29 mmol, 1.0 equiv) and of [6-(tert-butyl-diphenyl-silanyloxymethyl)-2-methyl-imidazo[1,2-a]pyrazin-3-yl]-oxo-acetic acid ethyl ester (158 mg, 0.32 mmol, 1.0 equiv) in anhydrous tetrahydrofuran (1.0 ml, dried over molecular sieves). The reaction mixture is stirred for 15 minutes at room temperature. It is then diluted with EtOAc and poured into a saturated aqueous NH$_4$Cl solution. After three extractions with EtOAc, the combined organic layers are dried over Na$_2$SO$_4$, filtered and concentrated in vacuo. The residue is dissolved in N,N-dimethylformamide (1.0 ml), treated with DBU (0.43 ml, 2.9 mmol, 10 equiv) and stirred under an atmosphere of argon for 5 minutes at 110° C. After cooling, the reaction mixture is diluted with water and extracted three times with EtOAc. The combined organic layers are washed with brine, dried over Na$_2$SO$_4$, filtered and concentrated in vacuo. Purification of the residue via flash chromatography (gradient of hexane/EtOAc 100:0 to 50:50) afford the title compound (60 mg, 34%). $^1$H NMR (400 MHz, d6-DMSO): δ=12.05 (br s, 1H), 11.25 (br s, 1H), 8.85 (d, J=1.2 Hz, 1H), 8.04 (s, 1H), 7.76 (s, 1H), 7.51-7.45 (m, 4H), 7.41-7.30 (m, 6H); 6.95 (t, J=7.1 Hz, 1H), 6.47 (t, J=7.4Hz, 1H), 5.76 (d, J=8.0 Hz, 1H), 4.59-4.47 (m, 2H), 2.82 (s, 3H), 0.92 (s, 9H). MS (ES+): 612 (M+H)+.

[6-(tert-Butyl-diphenyl-silanyloxymethyl)-2-methyl-imidazo[1,2-a]pyrazin-3-yl]-oxo-acetic acid ethyl ester

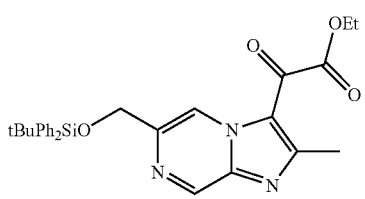

In a reaction tube, chloro-oxo-acetic acid ethyl ester (0.51 ml, 4.5 mmol, 7.2 equiv) is added to a solution of 6-(tert-butyl-diphenyl-silanyloxymethyl)-2-methyl-imidazo[1,2-a]pyrazine (250 mg, 0.62 mmol) in anhydrous THF (5 ml) under an atmosphere of argon. The tube is sealed under argon, and the reaction mixture is heated under microwave irradiation for 30 minutes at 120° C. After cooling, the reaction mixture is carefully poured into an aqueous solution of sodium carbonate. After three extractions with EtOAc, the combined organic layers are dried over $Na_2SO_4$, filtered and concentrated in vacuo. Purification via flash chromatography (hexane/EtOAc 4:1) affords the title compound (200 mg, 64%). $^1$H NMR (400 MHz, $d_6$-DMSO): δ=9.49 (d, J=1.4 Hz, 1H), 9.25 (d, J=1.4 Hz, 1H), 7.70-7.67 (m, 4H), 7.48-7.42 (m, 6H), 4.95(s, 2H), 4.47 (q, J=7.4Hz, 2H), 2.57 (s, 3H), 1.38 (t, J=7.4 Hz, 3H), 1.11 (s, 9H). MS (ES+): 502 (M+H)+.

6-(tert-Butyl-diphenyl-silanyloxymethyl)-2-methyl-imidazo[1,2-a]pyrazine

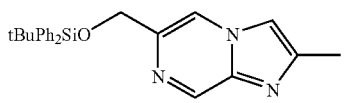

Bromoacetone (4.3 g, 31.4 mmol, 2.9 equiv) is added to a solution of 5-(tert-butyl-diphenyl-silanyloxymethyl)-pyrazin-2-ylamine (4.0 g, 10.7 mmol) in 1,2-dimethoxyethane (20 ml) and sulfolane (20 ml). The reaction mixture is stirred overnight at 50° C. Then a 10% aqueous solution of $NaHCO_3$ (30 ml) is added, and the mixture is heated to reflux for 1 hour. After cooling, the mixture is extracted three times with EtOAc. The combined organic layers are washed with brine, dried over $Na_2SO_4$, filtered and concentrated in vacuo. Purification by flash chromatography (hexane/EtOAc 3:1) affords the title compound (1.7 g, 40%). $^1$H NMR (400 MHz, $d_6$-DMSO): δ=8.78 (d, J=0.9 Hz, 1H), 8.43 (d, J=1.4 Hz, 1H), 7.92 (s, 1H), 7.63-7.61 (m, 4H); 7.41-7.35 (m, 6H), 4.72 (s, 2H), 2.34 (s, 3H), 1.00 (s, 9H). MS (ES+): 402 (M+H)+.

5-(tert-Butyl-diphenyl-silanyloxymethyl)-pyrazin-2-ylamine

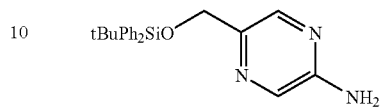

Imidazole (1.88 g, 27.3 mmol, 1.1 equiv) and tert-butyl-diphenylsilylchloride (6.5 ml, 27.3 mmol, 1.1 equiv) are added sequentially at room temperature to a solution of (5-amino-pyrazin-2-yl)-methanol (3.0 g, 24.0 mmol) in N,N-dimethylformamide (5 ml). The reaction mixture is stirred at room temperature for 3 hours, diluted with water, and extracted three times with EtOAc. The combined organic layers are washed with brine, dried over $Na_2SO_4$, filtered and concentrated in vacuo. The residue is purified via flash chromatography (gradient of hexane/EtOAc 3:1 to 1:1) to yield the title compound (6.0 g, 67%). $^1$H NMR (400 MHz, $d_6$-DMSO): δ=7.84 (d, J=1.4 Hz, 1H), 7.74 (d, J=1.4 Hz, 1H), 7.60-7.57 (m, 4H), 7.43-7.34 (m, 6H), 6.30 (br s, 2H), 4.56 (s, 2H), 0.94 (s, 9H). MS (ES+): 364 (M+H)+.

(5-Amino-pyrazin-2-yl)-methanol

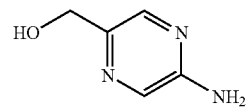

To a solution of 5-oxo-4,5-dihydro-pyrazine-2-carboxylic acid (10.0 g, 71.4 mmol) in SOCl2 (50 ml) are added a few drops of N,N-dimethylformamide. The clear solution is heated to reflux for 4 hours. After cooling, the solvent is removed in vacuo. The residue is dissolved in anhydrous dioxane (25 ml). This solution is then added dropwise at 0° C. to a solution of sodium borohydride (8.44 g, 214 mmol, 3.0 equiv) in water (120 ml). The reaction mixture is stirred at for 2 hours at 0° C., saturated with NaCl and rendered alkaline (pH=9) by the addition of a saturated aqueous KOH solution. After three extractions with EtOAc, the combined organic layers are dried over $Na_2SO_4$, filtered and concentrated in vacuo. The residue is dissolved in THF (10 ml) and concentrated aqueous $NH_3$ solution (25 ml). This mixture is heated to 170° C. in a stainless steel autoclave for 48 hours. After cooling, the solvent is removed in vacuo to yield the title compound (2.9 g, 28%) of sufficient purity for direct use in the next reaction. $^1$H NMR (400 MHz, $d_6$-DMSO): δ=7.91 (d, J=1.5 Hz, 1H), 7.81 (d, J=1.5 Hz, 1H), 6.26 (br s, 2H), 5.12 (t, J=5.4 Hz, 1H), 4.37 (d, J=5.4 Hz, 2H). MS (ES+): 126 (M+H)+.

By following the procedures of Example 20, the compounds of formula B wherein $R_a$, $R_b$, $R_1$ and $R_2$ are as indicated in Table 2 below may be obtained.

TABLE 2

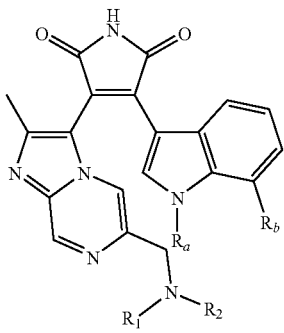

| | $R_1$ | $R_2$ | $R_a$ | $R_b$ | MS |
|---|---|---|---|---|---|
| 21. | $CH_3$ | $CH_3$ | $CH_3$ | H | $MH^+$ 416 |
| 22. | $CH_3$ | $CH_3$ | H | $CH_3$ | $MH^+$ 416 |
| 23. | $CH_3$ | $CH_3$ | H | H | $MH^+$ 401 |

EXAMPLE 24

3-(6-Dimethylaminomethyl-2-methyl-indolizin-3-yl)-4-(1H-indol-3-yl)-pyrrole-2,5-dione

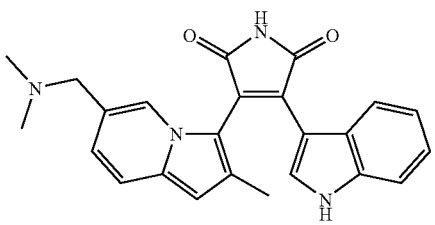

Potassium tert-butoxide (1.0 M in THF, 0.24 ml, 0.24 mmol, 3.0 equiv) is added dropwise at room temperature under an atmosphere of argon to a solution of (1H-indol-3-yl)-oxo-acetic acid methyl ester (19.2 mg, 0.090 mmol, 1.1 equiv) and of 2-(6-dimethylaminomethyl-2-methyl-indolizin-3-yl)-acetamide (20 mg, 0.08 mmol) in anhydrous tetrahydrofuran (1.0 ml, dried over molecular sieves). The reaction mixture is stirred for 30 minutes at room temperature. It is then diluted with EtOAc and poured into a saturated aqueous NH$_4$Cl solution. After three extractions with EtOAc, the combined organic layers are dried over Na$_2$SO$_4$, filtered and concentrated in vacuo. Purification of the residue via preparative HPLC affords the title compound (2 mg, 6%) as its trifluoroacetate salt. $^1$H NMR (400 MHz, d$_6$-DMSO): δ=11.78 (s, 1H), 10.91 (s, 1H), 9.51 (s, 1H), 8.33 (s, 1H), 7.99 (d, J=2.9 Hz, 1H), 7.54 (s, 1H), 7.35 (d, J=8.1 Hz, 1H), 7.03 (d, J=9.1 Hz, 1H), 6.95 (dt, J=8.0/1.2 Hz, 1H), 6.61 (dd, J=9.3/1.3 Hz, 1H), 6.52 (dt, J=8.1/1.0 Hz, 1H), 6.17 (d, J=8.0 Hz, 1H), 4.13 (s, 2H), 2.67 (s, 6H), 1.93 (s, 3H). MS (ES$^+$): 399 (M+H)$^+$.

2-(6-Dimethylaminomethyl-2-methyl-indolizin-3-yl)-acetamide

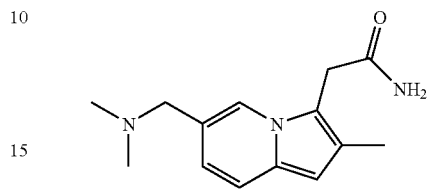

(6-Dimethylaminomethyl-2-methyl-indolizin-3-yl)-acetic acid tert-butyl ester (122 mg, 0.40 mmol) is dissolved in CH$_2$Cl$_2$ (10 ml) containing 5% of trifluoroacetic acid. The mixture is stirred for 14 hours at room temperature and then concentrated in vacuo. The residue is azeotroped twice with toluene, dissolved in N,N-dimethylformamide (2.0 ml) and treated with carbonyl diimidazole (76 mg, 0.44 mmol, 1.1 equiv). After 1 hour at room temperature, the volatiles are removed in vacuo, and the activated acid is taken up in concentrated aqueous ammonia (10 ml). The mixture is stirred for 30 minutes at room temperature and then concentrated in vacuo. The residue is purified via flash chromatography (CH$_2$Cl$_2$/MeOH 7:1) to afford the title compound (90 mg, 91%). $^1$H NMR (400 MHz, d6-DMSO): δ=7.31 (s, 1H), 7.27 (s, 1H), 6.75 (s, 1H), 6.61 (dd, J=9.3/1.5 Hz, 1H), 4.06 (s, 2H), 3.38 (s, 2H), 2.66 (s, 6H), 2.13 (s, 3H). MS (ES$^+$): 246 (M+H)$^+$.

(6-Dimethylaminomethyl-2-methyl-indolizin-3-yl)-acetic acid tert-butyl ester

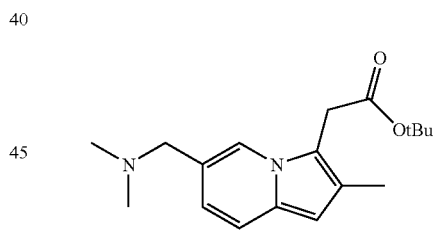

(6-Cyano-2-methyl-indolizin-3-yl)-acetic acid tert-butyl ester (500 mg, 1.76 mmol) is dissolved in a mixture of water (5.0 ml), pyridine (10 ml) and glacial acetic acid (5.0 ml). Sodium hypophosphite monohydrate (1.51 g, 14.1 mmol, 8 equiv) and Raney nickel (approx. 210 mg) are added at room temperature. The reaction mixture is heated to 75° C. for 1 h, cooled to room temperature, filtered through Celite and concentrated in vacuo. The residue is taken up in THF (5.0 ml) and treated with dimethylamine (5.3 M solution in EtOH, 1.66 ml, 8.8 mmol, 5.0 equiv). The mixture is stirred at room temperature for 18 hours. A solution of sodium cyanoborohydride (128 mg, 1.94 mmol, 1.1 equiv) in MeOH (0.5 ml) and glacial acetic acid (5.0 ml) are added, and the solution is stirred at room temperature for 2 hours. The reaction mixture is diluted with water and adjusted to pH 8-9 by the addition of concentrated aqueous NaHCO$_3$ solution. Extraction with EtOAc, washing with brine, drying over Na$_2$SO$_4$ and removal of solvent affords the crude reaction product. Purification via flash chromatography (EtOAc/hexane 4:1, +0.2% NEt₃) yields the title compound (122 mg, 23%). ¹H NMR (400 MHz, CDCl₃): δ=7.62 (s, 1H), 7.20 (d, J=9.0 Hz, 1H), 7.00 (s, 1H), 6.56 (dd, J=9.3/1.5 Hz, 1H), 3.52 (s, 2H), 3.22 (s, 2H), 2.19 (s, 6H), 1.35 (s, 9H). MS (ES⁺): 303 (M+H)⁺.

(6-Cyano-2-methyl-indolizin-3-yl)-acetic acid tert-butyl ester

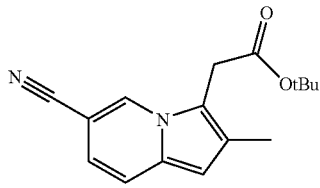

Under an atmosphere of argon, 3-bromo-2-methyl-indolizine-6-carbonitrile (500 mg, 2.12 mmol), Pd₂(dba)₃ (19.5 mg, 21.2 μmol, 0.01 equiv), 1,2,3,4,5-pentaphenyl-1-(di-tert-butylphosphino)ferrocene (15.1 mg, 21.2 1μmol, 0.01 equiv) and the isolated, recrystallized Reformatsky reagent prepared from tert-butyl bromoacetate (609 mg, 2.33 mmol, 1.1 equiv) are placed in a 50-ml round bottom flask. After three careful degassing cycles, anhydrous THF (8 ml) is added, and the reaction mixture is stirred at room temperature. After 1 hour at room temperature, TLC analysis indicated incomplete conversion. Consequently, additional portions of the palladium salt, the phosphino ligand and the Reformatsky reagent are added (same quantities as above). After 1 additional hour, reagents are added again, to achieve complete conversion after a total reaction time of 4 hours at room temperature. The reaction mixture is diluted with water, and extracted three times with EtOAc. The combined organic layers are washed with brine, dried over Na₂SO₄, filtered, and concentrated in vacuo. Purification of the residue via flash chromatography (hexane/EtOAc 6:1) affords the title compound (390 mg, 68%). ¹H NMR (400 MHz, CDCl₃): δ=8.22 (t, J=1.2 Hz, 1H), 7.36 (d, J=9.2 Hz, 1H), 7.21 (s, 1H), 6.67 (dd, J=9.3/1.5 Hz, 1H). 3.61 (s, 2H), 2.31 (s, 3H), 1.44 (s, 9H). MS (ES⁺): 271 (M+H)⁺.

3-Bromo-2-methyl-indolizine-6-carbonitrile

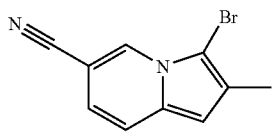

A solution of bromine (0.33 ml, 6.40 mmol. 1.0 equiv) in 10 ml of N,N-dimethylformamide is added under an atmosphere of argon at 0° C. to a solution of 2-methyl-indolizine-6-carbonitrile (1.0 g, 6.40 mmol) in 5 ml of N,N-dimethylformamide. The reaction mixture is heated in a microwave for 3 minutes at 80° C. After cooling, the reaction mixture is diluted with EtOAc and concentrated aqueous NaHCO₃ solution. The aqueous phase is extracted three times with EtOAc. The combined organic layers are washed with brine, dried over Na₂SO₄, filtered, and concentrated in vacuo. Purification of the residue via flash chromatography (hexane/EtOAc 4:1, +0.2% NEt₃) affords the title compound (1.0 g, 53%). ¹H NMR (400 MHz, d₆-DMSO): δ=8.97 (t, J=1.4 Hz, 1H), 7.56 (s, 1H), 7.28 (d, J=9.3 Hz, 1H), 6.87 (dd, J=9.3/1.5 Hz, 1H), 2.15 (d, J=1.0 Hz, 3H). MS (ES⁺): 236 (M+H)³⁰.

2-Methyl-indolizine-6-carbonitrile

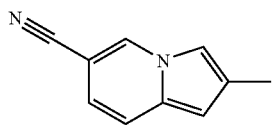

1-Bromo-propan-2-one (2.26 ml) is added under an atmosphere of argon to a solution of 5-cyano-2-methylpyridine (5.0 g, 41.9 mmol) in sulfolane (30 ml). The reaction mixture is stirred for 48 hours at 45° C., then diluted with EtOAc. The precipitated salt is filtered off and dissolved in water (50 ml). The aqueous solution is washed with EtOAc, then a 10% aqueous solution of NaHCO₃ (30 ml) is added, and the mixture is heated to reflux for 1 hour. After cooling, the reaction mixture is filtered, and the filtrate is extracted three times with EtOAc. The combined organic layers are dried over Na₂SO₄, filtered, and concentrated in vacuo. The residue is purified via flash chromatography (hexane/EtOAc 8:1, +0.2% NEt₃) to afford the title compound (5.50 g, 84%). ¹H NMR (400 MHz, d₆-DMSO): δ=9.10-9.09 (m, 1H), 7.59 (s, 1H), 7.55 (d, J=9.0 Hz, 1H), 6.90 (dd, J=9.3/1.7 Hz, 1H), 6.55 (s, 1H) 2.39 (s, 3H). MS (ES⁺): 157 (M+H)⁺.

By following the procedures of Example 24, the compounds of formula C wherein $R_a$, $R_b$, $R_1$ and $R_2$ are as indicated in Table 3 below may be obtained.

TABLE 3

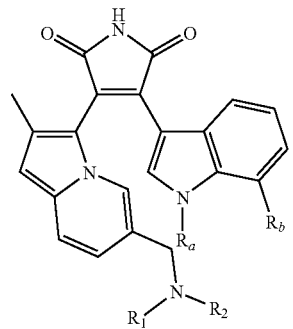

| | $R_1$ | $R_2$ | $R_a$ | $R_b$ | MS |
|---|---|---|---|---|---|
| 25 | CH₃ | CH₃ | H | CH₃ | MH⁺ 413 |

EXAMPLE 26

3-(6-Dimethylaminomethyl-imidazo[1,2-a]pyridin-3-yl)-4-(1H-indol-3-yl)-pyrrole-2,5-dione

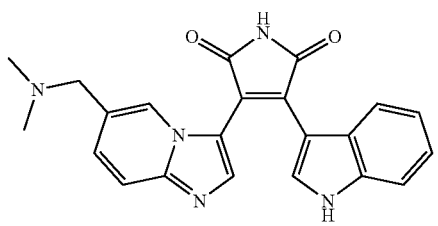

Potassium tert-butoxide (1.0 M in THF, 0.55 ml, 0.55 mmol, 2.7 equiv) is added dropwise at room temperature under an atmosphere of argon to a solution of (1H-indol-3-yl)-oxo-acetic acid methyl ester (45 mg, 0.22 mmol, 1.1 equiv) and of 2-(6-dimethylaminomethyl-imidazo[1,2-a]pyridin-3-yl)-acetamide (50 mg, 0.20 mmol) in anhydrous tetrahydrofuran (5.0 ml, dried over molecular sieves). The reaction mixture is stirred for 30 minutes at 0° C. It is then diluted with EtOAc and poured into a saturated aqueous NH$_4$Cl solution. After three extractions with EtOAc, the combined organic layers are dried over Na$_2$SO$_4$, filtered and concentrated in vacuo. The residue is dissolved in N,N-dimethylformamide (5 ml), treated with DBU (0.27 ml, 1.8 mmol, 8.9 equiv) and heated to 110° C. for 10 minutes. After cooling, the reaction mixture is diluted with water and extracted three times with CH$_2$Cl$_2$. The combined organic layers are ished with brine, dried over Na$_2$SO$_4$, filtered and concentrated in vacuo. Purification of the residue via preparative HPLC affords the title compound (34 mg, 43%) as its trifluoroacetate salt. $^1$H NMR (400 MHz, d$_6$-DMSO): δ=12.11 (s, 1H), 11.27 (s, 1H), 9.47 (br s, 1H), 8.21 (d, J=2.9 Hz, 1H), 8.05 (s, 1H), 7.78-7.76 (m, 2H), 7.73 (d, J=8.0 Hz, 1H), 7.29 (dd, J=8.0/4.0 Hz, 1H), 6.94 (t, J=8.0 Hz, 1H), 6.49 (t, J=8.0 Hz, 1H), 5.95 (d, J=8.0 Hz, 1H), 3.48-3.40 (m, 2H), 2.16 (s, 6H). MS (ES$^+$): 386 (M+H)$^+$.

2-(6-Dimethylaminomethyl-imidazo[1,2-a]pyridin-3-yl)-acetamide

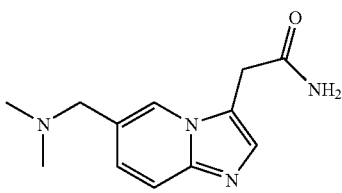

Lithium hydroxide monohydrate (55 mg, 1.31 mmol, 1.5 equiv) is added to a solution of (6-dimethylaminomethyl-imidazo[1,2-a]pyridin-3-yl)-acetic acid ethyl ester (240 mg, 0.87 mmol) in dioxane (10 ml) and water (10 ml). After 1 hour at room temperature, the reaction mixture is concentrated in vacuo. The residue is taken up in N,N-dimethylformamide (10 ml) and treated with trifluoroacetic acid (0.34 ml, 4.5 mmol, 4.5 equiv). Carbonyldiimidazole (167 mg, 0.98 mmol, 1.0 equiv) is added, and the mixture is stirred at room temperature for 1 hour. After removal of the solvent, concentrated aqueous ammonia (10 ml) is added to the activated acid. The mixture is stirred at room temperature for 30 minutes. Volatiles are removed in vacuo, and purification of the residue via flash chromatography (CH$_2$Cl$_2$/MeOH 7:3) affords the title compound (186 mg, 76%). $^1$H NMR (400 MHz, d$_4$-MeOH): δ=8.31 (s, 1H), 7.55 (d, J=9.0 Hz, 1H), 7.49 (s, 1H), 7.35 (dd, J=9.0/1.5 Hz, 1H), 3.95 (s, 2H), 3.71 (s, 2H), 2.42 (s, 6H). MS (ES$^+$): 233 (M+H)$^+$.

(6-Dimethylaminomethyl-imidazo[1,2-a]pyridin-3-yl)-acetic acid ethyl ester

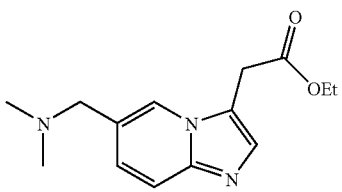

(6-Formyl-imidazo[1,2-a]pyridin-3-yl)-acetic acid ethyl ester (770 mg, 3.15 mmol) is dissolved in THF (10 ml) and treated with an excess of dimethylamine. The reaction mixture is stirred for 16 hours at room temperature in a stainless steel autoclave. A solution of sodium cyanoborohydride (229 mg, 3.46 mmol, 1.1 equiv) in MeOH (1.0 ml) and glacial acetic acid (1.1 ml) are added, and the solution is stirred for 1 hour at 60° C. The reaction mixture is diluted with water and adjusted to pH 8-9 by the addition of concentrated aqueous NaHCO$_3$ solution. Extraction with EtOAc, washing with brine, drying over Na$_2$SO$_4$ and removal of solvent affords the crude reaction product. Purification via flash chromatography (EtOAc/cyclohexane 4:1, +0.2% NEt$_3$) yields the title compound (242 mg, 29%). $^1$H NMR (400 MHz, CDCl$_3$): δ=7.76-7.74 (m, 1H), 7.35 (dd, J=9.3/1.0 Hz, 1H), 7.31 (s, 1H), 6.99 (dd, J=9.1/1.7 Hz, 1H), 3.95 (q, J=7.1 Hz, 2H), 3.71 (s, 2H), 3.23 (s, 2H), 2.06 (s, 6H), 1.03 (t, J=7.1 Hz, 3H). MS (ES$^+$): 262 (M+H)$^+$.

(6-Formyl-imidazo[1,2-a]pyridin-3-yl)-acetic acid ethyl ester

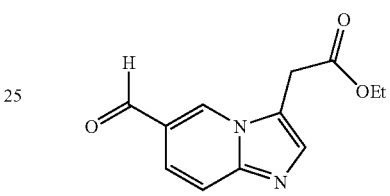

(6-Cyano-imidazo[1,2-a]pyridin-3-yl)-acetic acid ethyl ester (1.80 g, 7.46 mmol) is dissolved in a mixture of water (5.0 ml), pyridine (10 ml) and glacial acetic acid (5.0 ml). Sodium hypophosphite monohydrate (6.03 g, 56.4 mmol, 8 equiv) and Raney nickel (approx. 1.2 g) are added at room temperature. The reaction mixture is heated to 75° C. for 1 h, cooled to room temperature and filtered through Celite. The filtrate is extracted three times with EtOAc. The combined organic layers are washed with brine, dried over Na$_2$SO$_4$, filtered and concentrated in vacuo. Purification of the residue via flash chromatography (cylcohexane/EtOAc 1:1, +0.1% NEt3) affords the title compound (770 mg, 42%). $^1$H NMR (400 MHz, CDCl$_3$): δ=10.01 (s, 1H), 8.69 (s, 1H), 7.73 (s, 1H), 7.72 (s, 1H), 7.69 (s, 1H), 4.23 (q, J=7.1 Hz, 2H), 4.04 (s, 2H), 1.30 (t, J=7.4 Hz, 3H). MS (ES$^+$): 233 (M+H)$^+$.

(6-Cyano-imidazo[1,2-a]pyridin-3-yl)-acetic acid ethyl ester

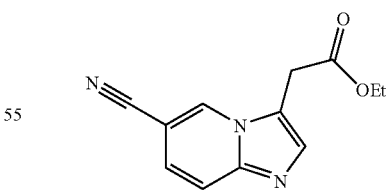

2-Amino-5-cyanopyridine (5.0 g, 39.9 mmol) and ethyl-(E)-4-oxobutenoate (5.92 g, 43.9 mmol, 1.1 equiv) are dissolved in acetonitrile (25 ml). The solution is heated for 14 hours at 90° C. After cooling, volatiles are removed in vacuo, and the residue is purified by flash chromatography (gradient hexane/EtOAc 100:0 to 50:50) to afford the title compound (2.77 g, 29%). $^1$H NMR (400 MHz, d$_6$-DMSO): δ=9.17-9.15 (m, 1H), 7.60 (dd, J=9.3/1.0 Hz, 1H), 7.54 (s, 1H), 7.37 (dd, J=9.3/1.7 Hz, 1H), 4.07 (s, 2H), 3.99 (q, J=7.4 Hz, 2H), 1.07 (t, J=7.1 Hz, 3H). MS (ES+): 230 (M+H)+.

EXAMPLE 27

3-(6-Dimethylaminomethyl-2-methyl-imidazo[1,2-a]pyridin-3-yl)-4-(1H-indol-3-yl)-pyrrole-2,5-dione

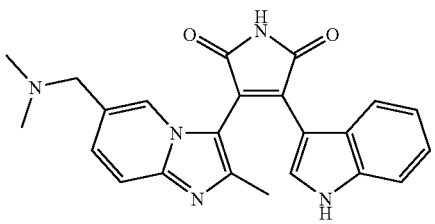

Methanesulfonic anhydride (45 mg, 0.31 mmol, 4.0 equiv) is added at room temperature under an atmosphere of argon to a solution of 3-(6-hydroxymethyl-2-methyl-imidazo[1,2-a]pyridin-3-yl)-4-(1H-indol-3-yl)-pyrrole-2,5-dione (30 mg, 0.08 mmol) and of pyridine (0.011 ml, 0.15 mmol, 2.0 equiv) in anhydrous THF (5.0 ml). The reaction mixture is stirred for 2 hour at room temperature. After addition of 1 M aqueous hydrochloric acid, the aqueous phase is extracted three times with EtOAc. The combined organic layers are washed with brine, dried over $Na_2SO_4$, filtered and concentrated in vacuo. The mesylate is dissolved in a solution of dimethylamine in EtOH (33%, 5.0 ml), and the reaction mixture is stirred at room temperature for 10 minutes. Water is added, and the mixture is extracted three times with EtOAc. The combined organic layers are washed with brine, dried over $Na_2SO_4$, filtered, and concentrated in vacuo. Purification by preparative HPLC yields the title compound as its trifluoroacetate salt (24 mg, 77%). $^1$H NMR (400 MHz, d$_6$-DMSO): δ=12.12 (s, 1H), 11.26 (s, 1H), 8.18 (d, J=3.2 Hz, 1H), 8.03 (s, 1H), 7.69 (d, J=9.0 Hz, 1H), 7.35 (dd, J=9.3/1.2 Hz, 1H), 7.31 (d, J=8.0 Hz, 1H), 6.93 (dt, J=7.1/1.0 Hz, 1H), 6.50 (dt, J=7.6/1.0 Hz, 1H), 5.89 (d, J=8.1 Hz, 1H), 4.11 (d, J=12.8 Hz, 1H), 3.91 (d, J=11.7 Hz, 1H), 2.48 (br s, 3H), 2.21 (s, 3H), 2.00 (br s, 3H). (ES+): 400 (M+H)+.

3-(6-Hydroxymethyl-2-methyl-imidazo[1,2-a]pyridin-3-yl)-4-(1H-indol-3-yl)-pyrrole-2,5-dione

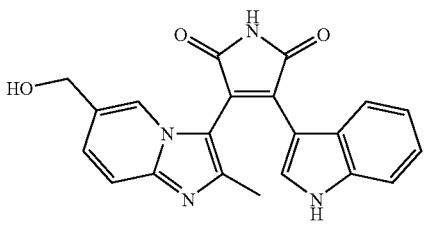

A 4 M aqueous solution of hydrochloric acid (5.0 ml) is added to 3-[6-(tert-butyl-diphenyl-silanyloxymethyl)-2-methyl-imidazo[1,2-a]pyridin-3-yl]-4-(1H-indol-3-yl)-pyrrole-2,5-dione (180 mg, 0.29 mmol). The reaction mixture is stirred for 24 hours at 45° C. After removal of volatiles in vacuo, purification via flash chromatography ($CH_2Cl_2$/MeOH 95:5) affords the title compound (90 mg, 82%). $^1$H NMR (400 MHz, d$_6$-DMSO): δ=11.94 (s, 1H), 11.08 (s, 1H), 8.05 (s, 1H), 7.91 (s, 1H), 7.40 (d, J=9.0 Hz, 1H), 7.32 (d, J=8.1 Hz, 1H), 7.13 (dd, J=9.0/1.8 Hz, 1H), 6.92 (dt, J=7.8/1.0 Hz, 1H), 6.46 (dt, J=7.6/1.0 Hz, 1H), 5.90 (d, J=8.0 Hz, 1H), 5.14 (t, J=5.4 Hz, 1H), 4.25 (t, J=4.7 Hz, 2H), 1.84 (s, 3H). (ES+): 373 (M+H)+.

3-[6-(tert-Butyl-diphenyl-silanyloxymethyl)-2-methyl-imidazo[1,2-a]pyridin-3-yl]-4-(1H-indol-3-yl)-pyrrole-2,5-dione

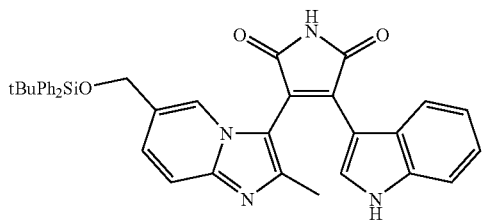

Potassium tert-butoxide (1.0 M in THF, 1.90 ml, 1.90 mmol, 3.0 equiv) is added dropwise at room temperature under an atmosphere of argon to a solution of (1H-Indol-3-yl)-oxo-acetic acid methyl ester (192 mg, 0.93 mmol, 1.5 equiv) and of 2-[6-(tert-butyl-diphenyl-silanyloxymethyl)-2-methyl-imidazo[1,2-a]pyridin-3-yl]-acetamide (300 mg, 0.62 mmol) in anhydrous tetrahydrofuran (5.0 ml, dried over molecular sieves). The reaction mixture is stirred for 30 minutes at 0° C., 30 minutes at room temperature and 1 hour at 45° C. It is then diluted with EtOAc and poured into a saturated aqueous NH$_4$Cl solution. After three extractions with EtOAc, the combined organic layers are dried over $Na_2SO_4$, filtered and concentrated in vacuo. Purification of the residue via flash chromatography (gradient of hexane/EtOAc 50:50 to 20:80) affords the title compound (180 mg, 45%). MS (ES+): 611 (M+H)+.

2-[6-(tert-Butyl-diphenyl-silanyloxymethyl)-2-methyl-imidazo[1,2-a]pyridin-3-yl]-acetamide

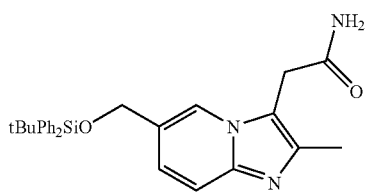

At −78° C., ammonia (25 ml) is added to [6-(tert-butyl-diphenyl-silanyloxymethyl)-2-methyl-imidazo[1,2-a]pyridin-3-yl]-acetic acid ethyl ester (950 mg, 1.85 mmol) in a glass autoclave. The reaction mixture is stirred at room temperature for 48 hours. After removal of volatiles, the residue is recrystallized from diethylether to afford the title compound (800 mg, 90%). MS (ES+): 458 (M+H)+.

[6-(tert-Butyl-diphenyl-silanyloxymethyl)-2-methyl-imidazo[1,2-a]pyridin-3-yl]-acetic acid ethyl ester

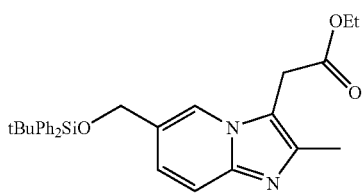

3-Bromo-4-oxo-pentanoic acid ethyl ester (1.77 g, 7.86 mmol, 2.0 equiv) and triethylamine (1.10 ml, 7.86 mmol, 2.0 equiv) are added to a solution of 5-(tert-butyl-diphenyl-silanyloxymethyl)-pyridin-2-ylamine in iso-propanol (10 ml). The reaction mixture is heated to reflux for 5 hours. After cooling, volatiles are removed in vacuo. The residue is taken up with water and EtOAc. The aqueous phase is extracted three times with EtOAc. The combined organic layers are washed with brine, dried over $Na_2SO_4$, filtered and concentrated in vacuo. Purification via flash chromatography (hexane/AcOEt 1:1 to 1:4) affords the title compound (1.10 g, 55%). MS (ES+): 487 (M+H)+.

5-(tert-Butyl-diphenyl-silanyloxymethyl)-pyridin-2-ylamine

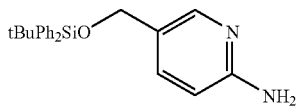

Ethyl-diisopropyl-amine (1.47 ml, 8.4 mmol, 1.1 equiv) and tert-butyl-diphenylsilyl chloride (2.22 ml, 8.4 mmol, 1.1 equiv) are added to a solution of (6-amino-pyridin-3-yl)-methanol (1.0 g, 7.65 mmol) in N,N-dimethylformamide (10 ml). The reaction mixture is stirred for 2 hours at room temperature, before it is diluted with water and extracted three times with EtOAc. The combined organic layers are washed with brine, dried over $Na_2SO_4$, filtered and concentrated in vacuo. The residue is purified via flash chromatography (EtOAc/hexane 1:1) to afford the title compound (2.10 g, 72%). $^1$H NMR (400 MHz, $d_6$-DMSO): δ=7.78 (s, 1H), 7.65-7.62 (m, 4H), 7.49-7.41 (m, 6H), 7.30 (dd, J=8.4/2.4 Hz, 1H), 6.42 (d, J=8.4 Hz, 1H), 5.87 (br s, 2H), 4.56 (s, 2H), 1.00 (s, 9H). MS (ES+): 363 (M+H)+.

(6-Amino-pyridin-3-yl)-methanol

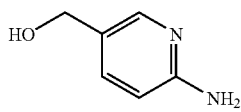

Concentrated sulfuric acid (0.95 ml, 17.2 mmol, 0.5 equiv) is added to a solution of 6-aminonicotinic acid (5.0 g, 34.4 mmol) in ethanol (50 ml). After heating to reflux for 16 hours, the reaction mixture is carefully poured into a concentrated aqueous $Na_2CO_3$ solution. The aqueous phase is extracted three times with EtOAc. The combined organic layers are washed with brine, dried over $Na_2SO_4$, filtered and concentrated in vacuo. The residue is dissolved in anhydrous THF (25 ml). At −60° C., lithium aluminium hydride (2.68 g, 68.6 mmol, 3.0 equiv) is carefully added. The mixture is warmed to 0° C., and then refluxed for 1 hour. After cooling, water (1.5 ml) and 5 N aqueous NaOH solution (1.5 ml) are added. The precipitate is filtered off, and the filtrate is concentrated in vacuo. The residue is purified via flash chromatography (EtOAc/MeOH 95:5) to afford the title compound (2.15 g, 72%). $^1$H NMR (400 MHz, $d_6$-DMSO): δ=7.82 (d, J=1.7 Hz, 1H), 7.32 (dd, J=8.3/2.5 Hz, 1H), 6.40 (dd, J=9.3/1.0 Hz, 1H), 5.77 (br s, 2H), 4.88 (t, J=5.5 Hz, 1H), 4.27 (d, J=5.5 Hz, 2H), MS (ES+): 125 (M+H)+.

By following the procedures of Examples 26 and 27, the compounds of formula D wherein $R_a$, $R_b$, $R_1$, $R_2$ and $R_3$ are as indicated in Table 4 below may be obtained.

TABLE 4

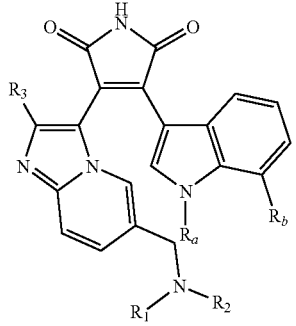

D

| | $R_3$ | $R_1$ | $R_2$ | $R_a$ | $R_b$ | MS |
|---|---|---|---|---|---|---|
| 28. | H | $CH_3$ | $CH_3$ | H | $CH_3$ | MH+ 400 |
| 29. | H | $CH_3$ | $CH_3$ | H | H | MH+ 386 |
| 30. | H | $CH_3$ | $CH_3$ | $CH_3$ | H | MH+ 400 |
| 31. | $CH_3$ | H | $CH_3$ | H | H | MH+ 386 |
| 32. | $CH_3$ | H | $CH_3$ | H | $CH_3$ | MH+ 400 |
| 33. | $CH_3$ | $CH_3$ | $CH_3$ | H | $CH_3$ | MH+ 414 |
| 34. | $CH_3$ | H | $CH_3$ | $CH_3$ | H | MH+ 400 |
| 35. | $CH_3$ | $CH_3$ | $CH_3$ | $CH_3$ | H | MH+ 414 |
| 36. | $CH_3$ | $CH_3$ | $CH_3$ | H | H | MH+ 400 |

EXAMPLES 37

3-(5-Dimethylaminomethyl-2-trifluoromethyl-1H-indol-3-yl)-4-(1H-indol-3-yl)-pyrrole-2,5-dione

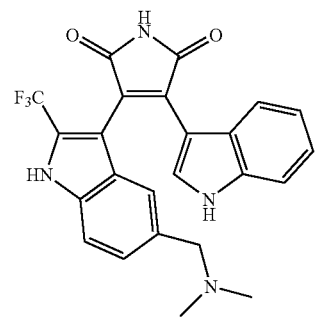

To a solution of 2-(5-dimethylaminomethyl-2-trifluoromethyl-1H-indol-3-yl)-acetamide (59.2 mg, 0.198 mmol) and (1H-indol-3-yl)-oxo-acetic acid methyl ester (60.3 mg, 0.297 mmol) in anhydrous THF (4.0 mL) is added dropwise a 1 M solution of t-BuOK in THF (0.989 mL) under an argon atmosphere at 0° C., followed by the addition of DMF(1.0 mL). The resulting deep red reaction mixture is stirred for 1 h at room temperature, diluted with EtOAc, washed with a saturated aqueous $NH_4Cl$ solution and washed with brine. The aqueous layer is extracted with EtOAc and the combined organic phases are dried over $Na_2SO_4$, filtered and concentrated at reduced pressure to afford a red solid. The crude product is dissolved in DMF (1.0 mL), DBU (300 1μL) is added, and the thus obtained solution is heated for 5 min. at 100° C. After cooling, the reaction mixture is diluted with EtOAc and washed with brine. The aqueous layer is extracted with EtOAc and the combined organic phases are dried over $Na_2SO_4$, filtered and concentrated at reduced pressure to afford a red solid. Purification by flash column chromatography (silica gel, EtOAc/acetic acid/water 8:1:1) affords the title compound as an orange solid (11 mg, 0.024 mmol, 12%). $^1$H NMR (400 MHz, DMSO-$d_6$, 298 K): δ=12.54 (bs, 1H), 11.78 (bs, 1H), 11.06 (bs, 1H), 7.95 (d, J=2.9 Hz, 1H), 7.36 (d, J=8.5 Hz, 1H), 7.25 (d, J=8.1 Hz, 1H), 7.06 (d, J=8.4 Hz, 1H), 6.88 (t, J=8.1 Hz, 1H), 6.84 (s, 1H), 6.51 (t, J=8.1 Hz, 1H), 6.45 (d, J=8.4 Hz, 1H), 3.10 (AB-system: δA=3.24 (d, $J_{AB}$=−12.4 Hz, 1H), δB=2.97 (d, $J_{AB}$=−12.4 Hz, 1H), 1.70 (s, 6H). MS (ES$^+$): 453 $(M(C_{24}H_{19}F_3N_4O_2)+H)^+$.

2-(5-Dimethylaminomethyl-2-trifluoromethyl-1H-indol-3-yl)-acetamide

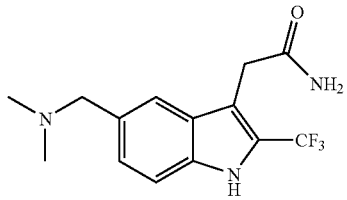

A solution of (5-dimethylaminomethyl-2-trifluoromethyl-1H-indol-3-yl)-acetic acid ethyl ester (200 mg, 0.609 mmol) in a mixture of methanol (5 mL) and liquid ammonia (30 mL) is stirred for 6 days in an autoclave at 80° C. After careful evaporation of the ammonia, the remaining solvent is evaporated in vacuo to afford the title compound as a red solid (182 mg, 0.609 mmol, 100%). $^1$H NMR (400 MHz, DMSO-$d_6$, 298 K): δ=12.18 (bs, 1H), 7.75 (s, 1H), 7.49 (d, J=8.6 Hz, 1H), 7.42 (bs, 1H), 7.35 (d, J=8.6 Hz, 1H), 6.95 (bs, 1H), 3.67 (s, 2H), 3.16 (s, 2H), 2.62 (s, 6H). MS (ES$^+$): 248 $(M(C_{14}H_{17}NO_3)+H)^+$. MS (ES$^+$): 300 $(M(C_{14}H_{16}F_3N_3O)+H)^+$.

(5-Dimethylaminomethyl-2-trifluoromethyl-1H-indol-3-yl)-acetic acid ethyl ester

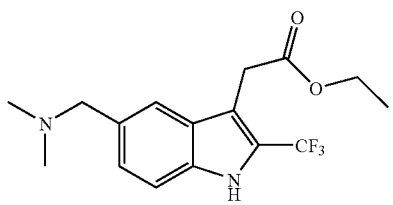

To a solution of (1-acetyl-5-bromomethyl-2-trifluoromethyl-1H-indol-3-yl)-acetic acid ethyl ester (378 mg, 0.93 mmol) in THF (16.0 mL) is added a 33% solution of dimethylamine in ethanol (8.0 mL). The resulting reaction mixture is stirred for 15 h at room temperature, followed by removal of the volatiles in vacuo. The residue is purified by flash column chromatography (silica gel, $CH_2Cl_2$/MeOH 9:1) to afford the title compound as a yellow solid (303 mg, 0.92 mmol, 99%). $^1$H NMR (400 MHz, CDCl$_3$, 298 K): δ=12.31 (s, 1H), 7.71 (s, 1H), 7.59 (d, J=8.6 Hz, 1H), 7.42 (d, J=8.6 Hz, 1H), 4.15 (q, J=7.1 Hz, 2H), 4.11 (s, 2H), 3.90 (s, 2H), 2.64 (s, 6H), 1.24 (t, J=7.1 Hz, 3H). MS (ES$^+$): 329 $(M(C_{16}H_{19}F_3N_2O_2)+H)^+$.

(1-Acetyl-5-bromomethyl-2-trifluoromethyl-1H-indol-3-yl)-acetic acid ethyl ester

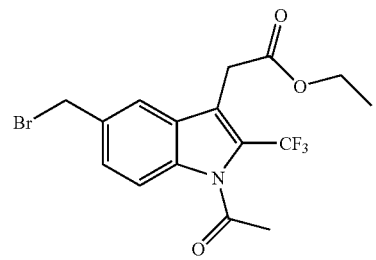

A mixture of (1-acetyl-5-methyl-2-trifluoromethyl-1H-indol-3-yl)-acetic acid ethyl ester (3.25 g, 9.94 mmol), AIBN (408 mg, 2.49 mmol) and N-bromosuccinimide (1.77 g, 9.94 mmol) in tetrachloromethane (50 mL) is heated to 80° C. for 2 h. After cooling to room temperature, the reaction mixture is filtered and the filtrate concentrated in vacuo. The crude product is purified by flash column chromatography (silica gel, cyclohexane/EtOAc 9:1) to afford the title compound as a yellow solid (2.44 g, 6.02 mmol, 61%). $^1$H NMR (400 MHz, CDCl$_3$, 298 K): δ=7.88 (s, J=8.8 Hz, 1H), 7.64 (s, 1H), 7.50 (d, J=8.8 Hz, 1H), 4.62 (s, 2H), 4.18 (q, J=7.1 Hz, 2H), 3.93 (s, 2H), 2.76 (s, 3H), 1.25 (t, J=7.1 Hz, 3H). MS (ES$^+$): 4.23 $(M(C_{16}H_{15}{}^{79}BrF_3NO_3)+H_2O)^+$.

(1-Acetyl-5-methyl-2-trifluoromethyl-1H-indol-3-yl)-acetic acid ethyl ester

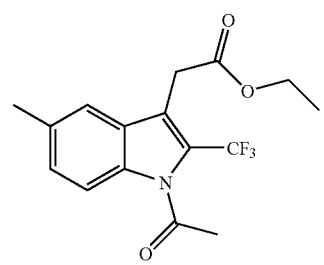

To a solution of (5-methyl-2-trifluoromethyl-1H-indol-3-yl)-acetic acid ethyl ester (4.90 g, 17.2 mmol) in DMF (25 mL) is added a suspension of 60% NaH in mineral oil (824 mg, 20.6 mmol). The reaction mixture is stirred for 1 h at room temperature. After cooling to 0° C. acetylchloride (1.84 mL, 25.8 mmol) is added dropwise. The resulting reaction mixture is stirred for 1 h at room temperature, quenched with an aqueous saturated NH$_4$Cl solution and partitioned between water and EtOAc. The layers are separated and the aqueous phase is extracted with EtOAc. The combined organic layers are washed with brine, dried over Na$_2$SO$_4$, filtered and concentrated at reduced pressure to afford a brown oil. Purification by flash column chromatography (silica gel, cyclohexane/EtOAc 95:5) affords the title compound as a yellow solid (2.89 g, 8.83 mmol, 51%). $^1$H NMR (400 MHz, CDCl$_3$, 298 K): δ=7.75 (d, J=8.8 Hz, 1H), 7.39 (s, 1H), 7.28 (d, J=8.8 Hz, 1H), 4.17 (q, J=7.1 Hz, 2H), 3.91 (q, J=2.2 Hz, 2H), 2.75 (s, 3H), 2.46 (s, 3H), 1.24 (t, J=7.1 Hz, 3H). MS (ES$^+$): 3.45 (M(C$_{16}$H$_{16}$F$_3$NO$_3$)+H$_2$O)$^+$.

(5-Methyl-2-trifluoromethyl-1H-indol-3-yl)-acetic acid ethyl ester

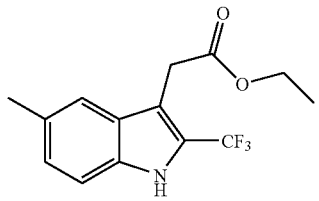

A mixture of 5,5,5-trifluoro-4-oxo-pentanoic acid ethyl ester (6.00 g, 30.3 mmol) and p-tolylhydrazine hydrochloride (4.80 g, 30.3 mmol) in ethanol (25 mL) is cooled to 0° C. The solution is saturated with HCl gas and heated at reflux for 18 h under an argon atmosphere. After cooling to room temperature the reaction mixture is concentrated by rotary evaporation. The residue is partitioned between a saturated aqueous NaHCO$_3$ solution and EtOAc. The layers are separated and the aqueous phase is extracted with twice with EtOAc. The combined organic layers are washed with brine, dried over Na$_2$SO$_4$, filtered and concentrated at reduced pressure to afford a brown oil. Purification by flash column chromatography (silica gel, gradient of cyclohexane/EtOAc 10:0 to 9:1) affords the title compound as orange crystals (5.14 g, 18.0 mmol, 60%). $^1$H NMR (400 MHz, CDCl$_3$, 298 K): δ=12.17 (bs, 1H), 7.63 (s, 1H), 7.52 (d, J=8.3 Hz, 1H), 7.31 (d, J=8.3 Hz, 1H), 4.25 (q, J=7.1 Hz, 2H), 4.06 (s, 2H), 2.57 (s, 3H), 1.34 (t, J=7.1 Hz, 3H). MS (ES$^+$): 286 (M(C$_{14}$H$_{14}$F$_3$NO$_2$)+H)$^+$.

5,5,5-Trifluoro-4-oxo-pentanoic acid ethyl ester

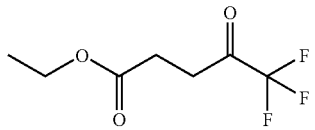

In a one-necked round-bottomed flask equipped with a distillation head and cooler, a mixture of 2-(2,2,2-trifluoro-acetyl)-succinic acid diethyl ester (54.6 g, 202 mmol) and boronic acid (12.5 g, 202 mmol) is heated to 170° C. Heating is continued for 4 h, during which time ethanol is gradually distilled off as it is formed. After cooling to room temperature, the reaction mixture is poured onto ice and extracted twice with EtOAc. The combined organic layers are washed with brine, dried over Na$_2$SO$_4$ and concentrated at reduced pressure to afford a brown oil. The crude product is purified by distillation (60° C., 10 mbar) to afford the title compound as a colorless liquid (17.3 g, 87.3 mmol, 43%). $^1$H NMR (400 MHz, CDCl$_3$, 298 K): δ=4.15 (q, J=7.1 Hz, 2H), 3.02 (t, J=6.4 Hz, 2H), 2.70 (t, J=6.4 Hz, 2H), 1.45 (t, J=7.1 Hz, 3H). MS (ES$^+$): 199 (M(C$_7$H$_9$F$_3$O$_3$)+H)$^+$.

2-(2,2,2-Trifluoro-acetyl)-succinic acid diethyl ester

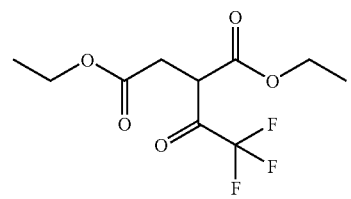

Under an argon atmosphere, trifluoroacetic acid ethyl ester (107 mL, 899 mmol) is added dropwise during 30 min. to a 60% suspension of NaH in mineral oil (22.6 g, 940 mmol). The resulting white suspension is heated to 60° C. and succinic acid ethyl ester (62.0 mL, 370 mmol) is added dropwise during 5 h. The reaction mixture is heated for 18 h at 65° C., cooled down to room temperature and carefully added to a mixture of ice (130 mg) and a 6 M aqueous H$_2$SO$_4$ solution (200 mL). The dark brown solution is extracted twice with TBME and the combined organic phases are washed with brine, dried over Na$_2$SO$_4$ and concentrated at reduced pressure to afford a brown oil. The crude product is purified by bulb-to-bulb distillation (100-120° C., 1 mbar) to afford the title compound as a pale yellow liquid (77.9 g, 288 mmol, 78%). MS (ES$^+$): 271 (M(C$_{10}$H$_{13}$F$_3$O$_5$)+H)$^+$. By following the procedures of Example 37, the compounds of formula E wherein R$_a$, R$_b$, R$_c$, R$_1$, R$_2$, R$_3$ and R$_4$ are as indicated in Table 5 below may be obtained.

TABLE 5

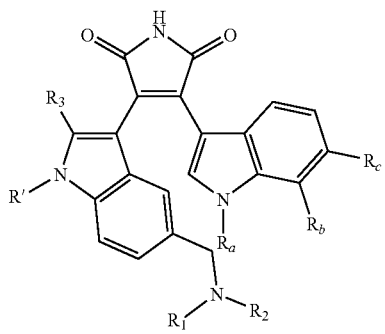

| | $R_3$ | R' | $R_1$ | $R_2$ | $R_a$ | $R_b$ | $R_c$ | MS |
|---|---|---|---|---|---|---|---|---|
| 38. | H | H | H | H | $CH_3$ | H | H | MH$^+$ 371 |
| 39. | H | H | H | H | H | H | H | MH$^+$ 357 |
| 40. | H | H | $CH_3$ | $CH_3$ | H | H | H | MH$^+$ 385 |
| 41. | H | H | $CH_3$ | $CH_3$ | $CH_3$ | H | H | MH$^+$ 399 |
| 42. | $CF_3$ | H | $CH_3$ | $CH_3$ | H | $CH_3$ | H | MH$^+$ 467 |
| 43. | $CH_3$ | H | $CH_3$ | $CH_3$ | $CH_3$ | H | H | MH$^+$ 413 |
| 44. | $CH_3$ | H | $CH_3$ | $CH_3$ | H | $CH_3$ | H | MH$^+$ 413 |
| 45. | $CH_3$ | H | $CH_3$ | $CH_3$ | H | H | $CH_3$ | MH$^+$ 413 |
| 46. | $CF_3$ | H | $CH_3$ | $CH_3$ | $CH_3$ | H | H | MH$^+$ 467 |
| 47. | $CF_3$ | H | $CH_3$ | $CH_3$ | H | H | $CH_3$ | MH$^+$ 467 |
| 48. | $CH_3$ | H | H | $CH_2CH_2F$ | $CH_3$ | H | H | MH$^+$ 431 |
| 49. | $CH_3$ | H | H | $CH_2CH_2F$ | H | $CH_3$ | H | MH$^+$ 431 |
| 50. | $CH_3$ | H | H | $CH_3$ | H | $CH_3$ | H | MH$^+$ 399 |
| 51. | $CH_3$ | H | H | $CH_3$ | $CH_3$ | H | H | MH$^+$ 399 |
| 52. | $CF_3$ | H | H | —$CHCH_2CH_2$— | H | H | $CH_3$ | MH$^+$ 479 |
| 53. | $CF_3$ | H | H | —$CHCH_2CH_2$— | $CH_3$ | H | H | MH$^+$ 479 |
| 54. | $CF_3$ | H | H | $CH_3$ | H | $CH_3$ | H | MH$^+$ 453 |
| 55. | $CF_3$ | H | H | $CH_3$ | $CH_3$ | H | H | MH$^+$ 453 |
| 56. | $CF_3$ | H | H | $CH_2CH(CH_2CH_2)$ | $CH_3$ | H | H | MH$^+$ 493 |
| 57. | $CH_3$ | $CH_2CH_2CH_2OH$ | $CH_3$ | $CH_3$ | H | $CH_3$ | H | MH$^+$ 471 |
| 58. | $CH_3$ | $CH_2CH_2CH_2OH$ | H | $CH_3$ | $CH_3$ | H | H | MH$^+$ 457 |
| 59. | $CH_3$ | $CH_2CH_2CH_2OH$ | $CH_3$ | $CH_3$ | $CH_3$ | H | H | MH$^+$ 471 |
| 60. | $CH_3$ | $CH_3$ | $CH_3$ | $CH_3$ | $CH_3$ | H | H | MH$^+$ 427 |
| 61. | $CH_3$ | $CH_3$ | $CH_3$ | $CH_3$ | H | $CH_3$ | H | MH$^+$ 427 |

EXAMPLES 62

3-(5-Dimethylaminomethyl-benzofuran-3-yl)-4-(1H-indol-3-yl)-pyrrole-2,5-dione

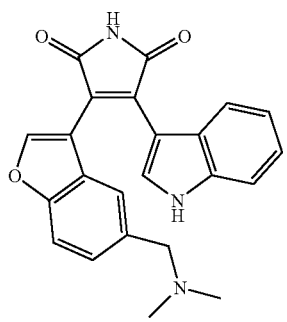

To a solution of 2-(5-dimethylaminomethyl-benzofuran-3-yl)-acetamide (91 mg, 0.39 mmol) and (1H-indol-3-yl)-oxo-acetic acid methyl ester (119 mg, 0.59 mmol) in anhydrous THF (5.0 mL) is added dropwise a 1 M solution of t-BuOK in THF (1.6 mL) under an argon atmosphere at 0° C. The resulting deep red reaction mixture is stirred for 5 min. at 0° C. and 30 min. at room temperature followed by partitioning between brine and EtOAc. The layers are separated and the aqueous layer is extracted twice with EtOAc. The combined organic layers are washed with brine, dried over $Na_2SO_4$, filtered and concentrated at reduced pressure to afford an orange solid. Purification by flash column chromatography (silica gel, EtOAc/acetic acid/water 7:1:1) affords the title compound as an orange solid (91.4 mg, 0.237 mmol, 63%). $^1$H NMR (400 MHz, DMSO-$d_6$, 298 K): δ=11.90 (bs, 1H), 11.06 (bs, 1H), 8.28 (s, 1H), 7.89 (s, 1H), 7.47 (d, J=8.4 Hz, 1H), 7.33 (d, J=8.2 Hz, 1H), 7.06 (d, J=8.4 Hz, 1H), 6.94 (t, J=8.2 Hz, 1H), 6.82 (d, J=8.1 Hz, 1H), 6.63 (d, J=8.2 Hz, 1H), 6.60 (s,1H), 2.98 (s, 2H), 1.69 (s, 6H). MS (ES$^+$): 386 (M($C_{23}H_{19}N_3O_3$)+H)$^+$.

2-(5-Dimethylaminomethyl-benzofuran-3-yl)-acetamide

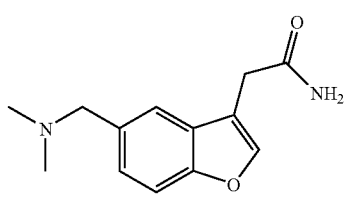

A solution of (5-dimethylaminomethyl-benzofuran-3-yl)-acetic acid methyl ester (170 mg, 0.69 mmol) in a mixture of methanol (15 mL) and liquid ammonia (15 mL) is stirred for 2 days in an autoclave at 60° C. After careful evaporation of the ammonia, the remaining solvent is evaporated in vacuo to afford the title compound as a yellow oil (160 mg, 0.69 mmol, 100%). MS (ES+): 233 (M($C_{13}H_{16}N_2O_2$)+H)+.

(5-Dimethylaminomethyl-benzofuran-3-yl)-acetic acid methyl ester

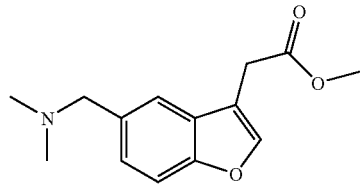

To a solution of (5-bromomethyl-benzofuran-3-yl)-acetic acid methyl ester (198 mg, 0.70 mmol) in THF (4.0 mL) is added a 5.6 M solution of dimethylamine in ethanol (1.0 mL). The resulting reaction mixture is stirred for 2 h at room temperature, filtered through a microfilter (25 μm) and the filtrate concentrated at reduced pressure to afford the title compound as a yellow oil (170 mg, 0.69 mmol, 98%). $^1$H NMR (400 MHz, CDCl$_3$, 298 K): δ=7.56 (s, 1H), 7.45 (s, 1H), 7.36 (d, J=8.6 Hz, 1H), 7.23 (d, J=8.6 Hz, 1H), 3.66 (s, 3H), 3.64 (s, 2H), 3.52 (s, 2H), 2.24 (s, 3H). MS (ES+): 248 (M($C_{14}H_{17}NO_3$)+H)+.

(5-Bromomethyl-benzofuran-3-yl)-acetic acid methyl ester

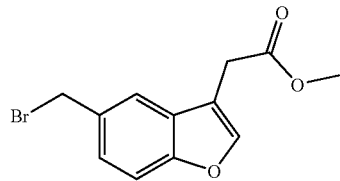

To a solution of 5-methyl-benzofuran-3-yl)-acetic acid methyl ester (3.1 g, 15.0 mmol) in tetrachloromethane (200 mL) is added N-bromosuccinimide (2.80 g, 15.0 mmol). The reaction mixture is heated to 45° C. for 1.5 h under simultaneous irradiation by a 300 W UV lamp. The reaction mixture is filtered and the filtrate concentrated in vacuo. The crude product is purified by flash column chromatography (silica gel, cyclohexane/EtOAc 98:2) to afford the title compound as yellow crystals (0.67 g, 2.37 mmol, 16%). $^1$H NMR (400 MHz, CDCl$_3$, 298 K): δ=7.68 (s, 1H), 7.61 (s, 1H), 7.47 (d, J=8.0 Hz, 1H), 7.38 (d, J=8.0 Hz, 1H), 4.67 (s, 2H), 3.77 (s, 3H), 3.73 (s, 2H).

(5-Methyl-benzofuran-3-yl)-acetic acid methyl ester

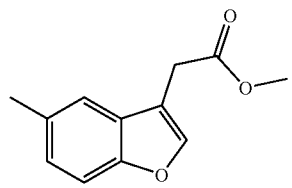

5-methyl-benzofuran-3-yl)-acetic acid (8.9 g, 47.0 mmol) is suspended in a 1.25 M solution of HCl in methanol (200 mL) and the resulting reaction mixture is heated for 2 h at reflux. After evaporation of the volatiles via rotary evaporation, the residue is purified by flash column chromatography (silica gel, cyclohexane/EtOAc 98:2) to afford the title compound as a colorless oil (8.80 g, 41.3 mmol, 92%). $^1$H NMR (400 MHz, CDCl$_3$, 298 K): δ=7.61 (s, 1H), 7.38 (d, J=8.3 Hz, 1H), 7.36 (s, 1H), 7.14 (d, J=8.3 Hz, 1H), 3.76 (s, 3H), 3.71 (s, 2H), 2.48 (s, 3H).

(5-Methyl-benzofuran-3-yl)-acetic acid

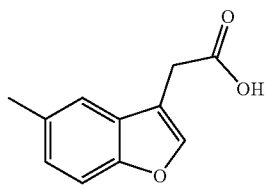

4-chloromethyl-6-methyl-chromen-2-one (10.4 g, 50.0 mmol) is suspended in a 1.0 M aqueous NaOH solution (400 mL). The reaction mixture is heated under reflux for 30 min. until a clear solution is obtained. The reaction mixture is cooled in an ice bath and carefully neutralized with a 2 M aqueous HCl solution (200 mL). More of a 2 M aqueous HCl solution is added until a white precipitate formed (pH <5). The precipitate is collected by suction filtration, washed with a small amount of an 1 M aqueous HCl solution and dried in vacuo at 50° C. to afford the title compound as a white powder (9.94 g, 47 mmol, 94%). $^1$H NMR (400 MHz, CDCl$_3$, 298 K): δ=7.63 (s, 1H), 7.39 (d, J=8.3 Hz, 1H), 7.36 (s, 1H), 7.14 (d, J=8.3 Hz, 1H), 3.76 (s, 2H), 2.48 (s, 3H).

4-Chloromethyl-6-methyl-chromen-2-one

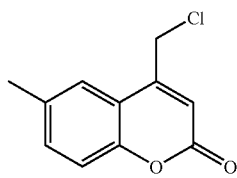

To a mixture of 4-methylphenol (21.6 g, 200 mmol) and 4-chloro-3-oxo-butyric acid ethyl ester (32.9 g, 200 mmol) is added dropwise during 30 min. at 0° C. a mixture of concentrated sulfuric acid (180 mL) and water (60 mL). The resulting clear solution is stirred for 18 h at room temperature, during which time a white precipitate is formed. The reaction mixture is poured over crushed ice (1 kg) and the formed precipitate is collected, washed with water and dried in vacuo at 50° C. to yield the title compound as a white powder (35.8 g, 172 mmol, 86%). $^1$NMR (400 MHz, CDCl$_3$, 298 K):

δ=7.45 (s, 1H), 7.40 (d, J=8.6 Hz, 1H), 7.29 (d, J=8.6 Hz, 1H), 6.58 (s, 1H), 4.69 (s, 1H), 2.46 (s, 3H).

EXAMPLE 63

3-(5-Dimethylaminomethyl-2-methyl-benzofuran-3-yl)-4-(7-methyl-1H-indol-3-yl)-pyrrole-2,5-dione

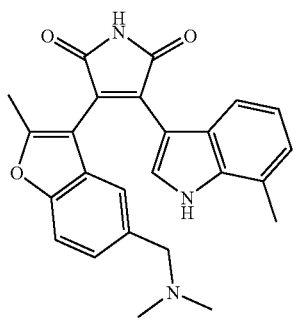

To a solution of 2-(5-dimethylaminomethyl-2-methyl-benzofuran-3-yl)-acetamide (111 mg, 0.406 mmol) and (7-methyl-1H-indol-3-yl)-oxo-acetic acid methyl ester (132 mg, 0.608 mmol) in anhydrous THF (4.0 mL) is added dropwise a 1 M solution of t-BuOK in THF (2.0 mL) at 0° C. under an argon atmposphere. The resulting deep red reaction mixture is stirred for 1 h at 0° C., diluted with EtOAc, washed with a saturated aqueous NH$_4$Cl solution and washed with brine. The combined aqueous phases are extracted with EtOAc and the combined organic phases are dried over Na$_2$SO$_4$, filtered and concentrated at reduced pressure to afford an orange solid. Purification by flash column chromatography (silica gel, EtOAc/acetic acid/water 7:1:1) affords the title compound as an orange solid (122 mg, 0.295 mmol, 73%). $^1$H NMR (400 MHz, DMSO-d$_6$, 298 K): δ=11.88 (bs, 1H), 11.07 (bs, 1H), 7.91 (s, 1H), 7.38 (d, J=8.3 Hz, 1H), 7.04 (d, J=8.3 Hz, 1H), 6.93 (s, 1H), 6.75 (d, J=6.8 Hz, 1H), 6.50 (t, J=7.5 Hz, 1H), 6.42 (d, J=7.8 Hz, 1H), 3.40-3.16 (m, 2H), 2.40 (s, 2H), 2.12 (s, 2H), 1.84 (s, 6H). MS (ES$^+$): 414 (M(C$_{25}$H$_{23}$N$_3$O$_3$)+H)$^+$.

2-(5-Dimethylaminomethyl-2-methyl-benzofuran-3-yl)-acetamide

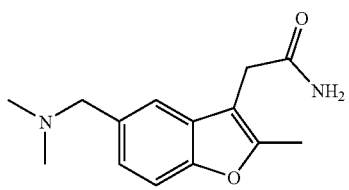

A solution of (5-dimethylaminomethyl-2-methyl-benzofuran-3-yl)-acetic acid ethyl ester (744 mg, 2.70 mmol) in a mixture of methanol (5 mL) and liquid ammonia (40 mL) is stirred for 3 days in an autoclave at 70° C. After careful evaporation of the ammonia, the remaining solvent is evaporated in vacuo to afford the title compound as beige solid (662 mg, 2.42 mmol, 90%). $^1$H NMR (400 MHz, DMSO-d$_6$, 298 K): δ=7.48 (bs, 1H), 7.42 (s, 1H), 7.36 (d, J=8.6 Hz, 1H), 7.11 (d, J=8.6 Hz, 1H), 6.93 (bs, 1H), 3.45 (s, 2H), 3.38 (s, 2H), 2.38 (s, 3H), 2.15 (s, 6H). MS (ES$^+$): 247 (M(C$_{16}$H$_{14}$O$_4$)+H)$^+$.

(5-Dimethylaminomethyl-2-methyl-benzofuran-3-yl)-acetic acid ethyl ester

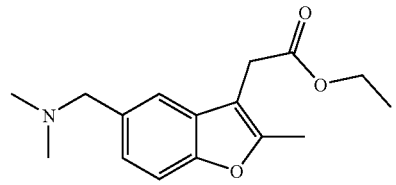

To a solution of (5-formyl-2-methyl-benzofuran-3-yl)-acetic acid ethyl ester (1.00 g, 4.06 mmol) in anhydrous ethanol (25 mL) is added a 5 M solution of dimethylamine in ethanol (4.1 mL). The resulting reaction mixture is stirred for 18 h at room temperature. Acetic acid (1.4 mL) and NaBH$_3$CN (279 mg, 4.22 mmol) are added and the resulting reaction mixture is heated at 50° C. for 4h. After cooling to room temperature the solvents are removed by rotary evaporation. The residue is taken up in water, basified (pH=8) with a saturated aqueous NaHCO$_3$ solution and extracted twice with EtOAc. The combined organic layers are dried over Na$_2$SO$_4$, filtered and concentrated in vacuo. The crude product is purified by flash column chromatography (silica gel, gradient of dichloromethane/methanol 10:0 to 9:1) to afford the title compound as a colorless oil (744 mg, 2.70 mmol, 67%). $^1$H NMR (400 MHz, CDCl$_3$, 298 K): δ=7.39 (s, 1H), 7.31 (d, J=8.3 Hz, 1H), 7.15 (d, J=8.3 Hz, 1H), 4.14 (q, J=7.1 Hz, 2H), 3.58 (s, 2H), 3.50 (s, 2H), 2.41 (s, 3H), 2.25 (s, 6H), 1.23 (t, J=7.1 Hz, 3H). MS (ES$^+$): 276 (M(C$_{16}$H$_{21}$NO$_3$)+H)$^+$.

(5-Formyl-2-methyl-benzofuran-3-yl)-acetic acid ethyl ester

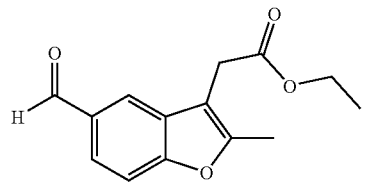

A mixture of (5-cyano-2-methyl-benzofuran-3-yl)-acetic acid ethyl ester (4.31 g, 17.7 mmol), NaPH$_2$O$_2$.H$_2$O (14.99 g, 141 mmol) and Raney nickel (3.06 g, 35.4 mmol) in a mixture of water (50 mL), acetic acid (50 mL) and pyridine (100 mL) is heated for 2 h at 100° C. under an argon atmosphere. After cooling to room temperature the reaction mixture is filtered over hyflo and the filtrate concentrated by rotary evaporation. The residue is partitioned between water and TBME, the layers are separated and the aqueous phase is extracted with TBME. The combined organic layers are washed with a 1 M aqueous HCl solution, a saturated aqueous NaHCO$_3$ solution and brine. After drying over Na$_2$SO$_4$ and evaporation of the solvent in vacuo the crude product is obtained as a brown oil. Further purification by flash column chromatography (silica gel gradient of cyclohexane/EtOAc 100:0 to 6:1) affords the title compound as colorless crystals (2.59 g, 10.5 mmol, 60%). $^1$H NMR (400 MHz, CDCl$_3$, 298 K): δ=10.08 (s, 1H), 8.07 (s, 1H), 7.82 (d, J=8.9 Hz, 1H), 7.52 (d, J=8.9 Hz, 1H), 4.19 (q, J=7.1 Hz, 2H), 3.66 (s, 2H), 2.49 (s, 3H), 1.27 (t, J=7.1 Hz, 3H). MS (ES$^+$): 247 (M(C$_{14}$H$_{14}$O$_4$)+H)$^+$.

(5-Cyano-2-methyl-benzofuran-3-yl)-acetic acid ethyl ester

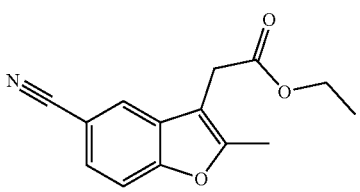

A mixture of (5-bromo-2-methyl-benzofuran-3-yl)-acetic acid ethyl ester (6.8 g, 22.9 mmol) and CuCN (3.1 g, 34.3 mmol) in anhydrous DMF (20 mL) is heated for 16 h at reflux (165° C.) under an argon atmosphere. After cooling to room temperature a solution of NaCN (5.8 g, 114 mmol) in water (30 mL) is added. The reaction mixture is partitioned between water and toluene, the layers are separated and the aqueous phase is extracted with toluene. The combined organic layers are washed with a 10% aqueous NaCN solution and brine, dried over Na$_2$SO$_4$, filtered and concentrated at reduced pressure to afford the title compound as a brown solid (4.31 g, 17.7 mmol, 77%). $^1$H NMR (400 MHz, CDCl$_3$, 298 K): δ=7.82 (d, J=1.7 Hz, 1H), 7.51-7.43 (m, 2H), 4.16 (q, J=7.1 Hz, 2H), 3.59 (s, 2H), 2.46 (s, 3H), 1.26 (t, J=7.1 Hz, 3H). MS (ES$^+$): 244 (M(C$_{14}$H$_{13}$NO$_3$)+H)$^+$.

(5-Bromo-2-methyl-benzofuran-3-yl)-acetic acid ethyl ester

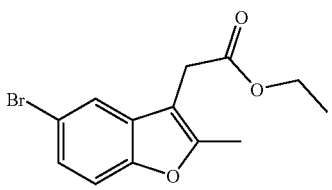

A mixture of 5-bromo-2-methyl-benzofuran-3-one (6.8 g, 29.9 mmol) and (triphenyl-phosphanylidene)-acetic acid ethyl ester (17.4 g, 44.9 mmol) in anhydrous toluene is heated for 40 h at 120° C. under an argon atmosphere. After cooling to room temperature the volatiles are removed by rotary evaporation. The residue is purified by flash column chromatography (silica gel, gradient of cyclohexane/EtOAc 100:0 to 90:10) to afford a mixture of two regioisomeric products. The product mixture (7.1 g, 31.3 mmol) is dissolved in a 1.25 M solution of HCl in ethanol and heated at reflux for 1 h. After cooling to room temperature the solvent is removed by rotary evaporation to yield the title compound as a pale yellow oil (6.9 g, 23.2 mmol, 78%). $^1$H NMR (400 MHz, CDCl$_3$, 298 K): δ=7.59 (d, J=2.0 Hz, 1H), 7.31-7.22 (m, 2H), 4.15 (q, J=7.1 Hz, 2H), 3.54 (s, 2H), 2.42 (s, 3H), 1.25 (t, J=7.1 Hz, 3H). MS (ES$^+$): 297 (M(C$_{13}$H$_{13}$$^{79}$BrO$_3$)+H)$^+$.

5-Bromo-2-methyl-benzofuran-3-one

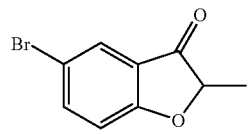

A suspension of acetic acid 5-bromo-2-methyl-benzofuran-3-yl ester (18.9 g, 70.4 mmol) in methanol (232 mL) and a I M aqueous HCl solution (44 mL) is heated under reflux (75° C.) for 7 h. After cooling to room temperature the reaction mixture is concentrated by rotary evaporation. The residue is diluted with water and extracted three times with diethyl ether. The combined organic layers are washed with water, brine, dried over Na$_2$SO$_4$, filtered and concentrated at reduced pressure to afford the title compound as a yellow oil (14.7 g, 64.7 mmol, 92%). MS (ES$^+$): 227 (M(C$_9$H$_7$$^{79}$BrO$_2$)+H)$^+$.

Acetic acid 5-bromo-2-methyl-benzofuran-3-yl ester

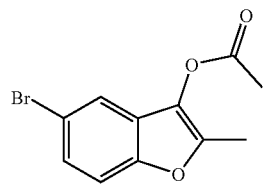

A mixture of 5-bromo-2-(1-carboxy-ethoxy)-benzoic acid (31.2 g, 108 mmol), acetic anhydride (216 mL) and anhydrous sodium acetate (21.8 g, 266 mmol) is heated under reflux (150° C.) for 4 h. After cooling to room temperature the reaction mixture is carefully quenched with ice-cold water (500 mL). A white precipitate is formed which is collected by suction filtration, thoroughly washed with water and dried in vacuo at 45° C. to afford the title compound as a white powder (19.0 g, 70.6 mmol, 65%). MS (ES$^+$): 269 (M(C$_{11}$H$_9$$^{79}$BrO$_3$)+H)$^+$.

5-Bromo-2-(1-carboxy-ethoxy)-benzoic acid

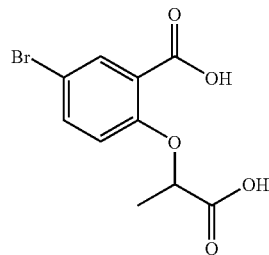

A solution of 5-bromo-2-(1-ethoxycarbonyl-ethoxy)-benzoic acid methyl ester (41.1 g, 124 mmol) in a mixture of THF (250 mL), MeOH (250 mL) and a 5 M aqueous NaOH solution (300 mL) is heated under reflux (85° C.) for 16 h. After cooling to room temperature the resulting suspension is concentrated by rotary evaporation. The residue is dissolved in water and acidified with an aqueous concentrated HCl solution under cooling with ice. The aqueous phase is extracted twice with EtOAc and the combined organic layers are washed with brine, dried over $Na_2SO_4$, filtered and concentrated at reduced pressure to afford the title compound as a beige solid (31.5 g, 109 mmol, 88%). $^1$H NMR (400 MHz, DMSO-$d_6$, 298 K): δ=13.04 (bs, 2H), 7.72 (d, J=2.7 Hz, 1H), 7.63 (dd, J=8.9, 2.7 Hz, 1H), 6.92 (d, J=8.9 Hz, 1H), 4.90 (q, J=6.6 Hz, 1H), 1.49 (d, J=6.6 Hz, 3H). MS (ES$^+$): 289 (M($C_{10}H_9{}^{79}BrO_5$)+H)$^+$.

5-Bromo-2-(1-ethoxycarbonyl-ethoxy)-benzoic acid methyl ester

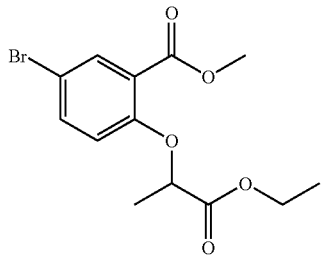

A mixture of 5-bromo-2-hydroxy-benzoic acid methyl ester (25.0 g, 103 mmol), 2-bromo-propionic acid ethyl ester (18.6 g, 103 mmol) and potassium carbonate (50.2 g, 360 mmol) in acetone (500 mL) is heated under reflux for 24 h. The reaction mixture is filtered, and the filtrate concentrated by rotary evaporation. The residue is dissolved in dichloromethane and washed twice with water. The organic layer is dried over $Na_2SO_4$, filtered and concentrated at reduced pressure to afford the title compound as a colorless oil (34.1 g, 103 mmol, 100%). $^1$H NMR (400 MHz, CDCl$_3$, 298 K): δ=7.91 (d, J=2.7 Hz, 1H), 7.49 (dd, J=8.8, 2.7 Hz, 1H), 6.75 (d, J=8.8Hz, 1H), 4.71 (q, J=6.8Hz, 1H), 4.20 (q, J=7.1 Hz, 2H), 3.88 (s, 3H), 1.65 (d, J=6.8 Hz, 3H), 1.23 (t, J=7.1 Hz, 3H). MS (ES$^+$): 331 (M($C_{13}H_{15}{}^{79}BrO_5$)+H)$^+$.

By following the procedures of Examples 62 and 63, the compounds of formula F wherein $R_a$, $R_b$, $R_c$, $R_1$, $R_2$, and $R_3$ are as indicated in Table 6 below may be obtained.

TABLE 6

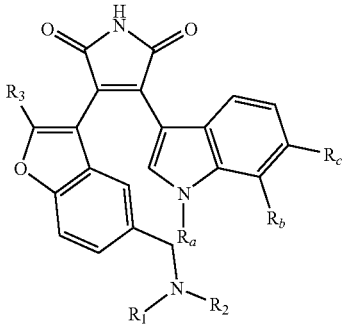

F

| | $R_3$ | $R_1$ | $R_2$ | $R_a$ | $R_b$ | $R_c$ | MS |
|---|---|---|---|---|---|---|---|
| 64. | H | CH$_3$ | CH$_3$ | H | H | H | MH$^+$ 386 |
| 65. | H | CH$_3$ | CH$_3$ | H | CH$_3$ | H | MH$^+$ 400 |

TABLE 6-continued

F

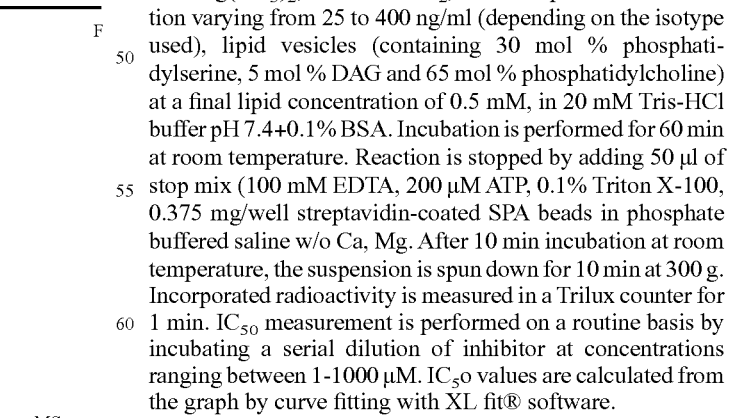

| | $R_3$ | $R_1$ | $R_2$ | $R_a$ | $R_b$ | $R_c$ | MS |
|---|---|---|---|---|---|---|---|
| 66. | H | H | —CHCH$_2$CH$_2$— | CH$_3$ | H | H | MH$^+$ 412 |
| 67. | H | H | —CHCH$_2$CH$_2$— | H | CH$_3$ | H | MH$^+$ 412 |
| 68. | H | H | —CHCH$_2$CH$_2$— | H | H | CH$_3$ | MH$^+$ 412 |
| 69. | H | H | CH$_3$ | CH$_3$ | H | H | MH$^+$ 386 |
| 70. | CH$_3$ | CH$_3$ | CH$_3$ | CH$_3$ | H | H | MH$^+$ 414 |
| 71. | CH$_3$ | CH$_3$ | CH$_3$ | H | CH$_3$ | H | MH$^+$ 414 |

The compounds of the invention, i.e. of formula (I), in free form or in pharmaceutically acceptable salt form, exhibit valuable pharmacological properties, e.g. inhibiting Protein Kinase C (PKC) activity, e.g. PKC isoforms like α, β, δ, ε, η or θ, in particular the isoforms α and β.

In another embodiment of the invention, the compounds of the invention, i.e. of formula (I), in free form or in pharmaceutically acceptable salt form inhibit T-cell activation and proliferation, e.g. by inhibiting production by T-cells or cytokines, e.g. IL-2, by inhibiting the proliferative response of T-cells to cytokines, e.g. IL-2, e.g. as indicated in vitro and in vivo tests and are therefore indicated for therapy.

A. In vitro

1. Protein Kinase C Assay

The compounds of the invention are tested for their activity on different PKC isoforms according to the following method. Assay is performed in a white with clear bottom 384-well microtiterplate with non-binding surface. The reaction mixture (25 μl) contains 1.5 μM of a tridecapeptide acceptor substrate that mimics the pseudo substrate sequence of PKC α with the Ala→Ser replacement, 10 μM $^{33}$P-ATP, 10 mM Mg(NO$_3$)$_2$, 0.2 mM CaCl$_2$, PKC at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 min at room temperature. Reaction is stopped by adding 50 μl of stop mix (100 mM EDTA, 200 μM ATP, 0.1% Triton X-100, 0.375 mg/well streptavidin-coated SPA beads in phosphate buffered saline w/o Ca, Mg. After 10 min incubation at room temperature, the suspension is spun down for 10 min at 300 g. Incorporated radioactivity is measured in a Trilux counter for 1 min. IC$_{50}$ measurement is performed on a routine basis by incubating a serial dilution of inhibitor at concentrations ranging between 1-1000 μM. IC$_{50}$ values are calculated from the graph by curve fitting with XL fit® software.

2. Protein Kinase C θ Assay

Human recombinant PKCθ is used under the assay conditions as described above. In this assay, compounds of the invention inhibit PKC θ with an IC$_{50}$≦1 μM.

3. Protein Kinase Cα Assay

Human recombinant PKCα is obtained from Oxford Biomedical Research and is used under the assay conditions as described under Section A.1 above. In this assay, compounds of the invention inhibit PKCα with an $IC_{50} \leq 1$ µM. For example, compound of example 6 inhibits PKCα with an $IC_{50}$ of 1.4 nM; compound of example 51 with an $IC_{50}$ of 0.3 nM.

4. Protein Kinase Cβ1 Assay

Human recombinant PKCβ1 is obtained from Oxford Biomedical Research and is used under the assay conditions as described under Section A.1 above. In this assay, compounds of the invention inhibit PKCβ1 with an $IC_{50} \leq 1$ µM. For example, compound of example 24 inhibits PKCβ1 with an $IC_{50}$ of 18.2 nM; compound of example 47 with an $IC_{50}$ of 0.9 nM.

5. Protein Kinase Cδ Assay

Human recombinant PKCδ is obtained from Oxford Biomedical Research and is used under the assay conditions as described under Section A.1 above. In this assay, compounds of the invention inhibit PKCδ with an $IC_{50} \leq 1$ µM.

6. Protein Kinase Cε Assay

Human recombinant PKCε is obtained from Oxford Biomedical Research and is used under the assay conditions as described under Section A.1 above. In this assay, compounds of formula (I), (II) and (III) inhibit PKCε with an $IC_{50} \leq 1$ µM.

7. Protein Kinase Cη Assay

Human recombinant PKCη is obtained from PanVera and is used under the assay conditions as described under Section A.1 above. In this assay, compounds of the invention inhibit PKCη with an $IC_{50} \leq 1$ µM.

8. CD28 costimulation Assay

The assay is performed with Jurkat cells transfected with a human interleukin-2 promoter/reporter gene construct as described by Baumann G et al. in Transplant. Proc. 1992;24:43-8, the β-galactosidase reporter gene being replaced by the luciferase gene (de Wet J., et al., Mol. Cell Biol. 1987, 7(2), 725-737). Cells are stimulated by solid phase-coupled antibodies or phorbol myristate acetate (PMA) and the $Ca^{++}$ ionophore ionomycin as follows. For antibody-mediated stimulation Microlite TM1 microtiter plates (Dynatech) are coated with 3 □g/ml goat anti-mouse IgG Fc antibodies (Jackson) in 55 µphosphate-buffered saline (PBS) per well for three hours at RT. Plates are blocked after removing the antibodies by incubation with 2% bovine serum albumin (BSA) in PBS (300 µl per well) for 2 hours at RT. After washing three times with 300 µl PBS per well, 10 ng/ml anti-T cell receptor antibodies (WT31, Becton & Dickinson) and 300 ng/ml anti-CD28 antibodies (15E8) in 50 µl 2% BSA/PBS are added as stimulating antibodies and incubated overnight at 4° C. Finally the plates are washed three times with 300 µl PBS per well. Seven three-fold serial dilutions of test compounds in duplicates in assay medium (RPMI 1640/10% fetal calf serum (FCS) containing 50 µM 2-mercaptoethanol, 100 units/ml penicillin and 100 µg/ml streptomycin) are prepared in separate plates, mixed with transfected Jurkat cells (clone K22 290_H23) and incubated for 30 minutes at 37° C. in 5% $CO_2$. 100 µl of this mixture containing $1 \times 10^5$ cells are then transferred to the antibody-coated assay plates. In parallel 100 µl are incubated with 40 ng/ml PMA and 2 µM ionomycin. After incubation for 5.5 hours at 37° C. in 5% $CO_2$, the level of luciferase is determined by bioluminescence measurement. The plates are centrifuged for 10 min at 500 g and the supernatant is removed by flicking. Lysis buffer containing 25 mM Tris-phosphate, pH 7.8, 2 mM DTT, 2 mM 1.2-diaminocyclohexane-N,N,N',N-tetraacetic acid, 10% (v/v) glycerol and 1% (v/v) Triton X-100 is added (20 pl per well). The plates are incubated at RT for 10 minutes under constant shaking. Luciferase activity is assessed with a bioluminescence reader (Labsystem, Helsinki, Finland) after automatic addition of 50 µl per well luciferase reaction buffer containing 20 mM Tricine, 1.07 mM $(MgCO_3)_4Mg(OH)_{2\times5}$ $H_2O$, 2.67 mM $MgSO_4$, 0.1 mM EDTA, 33.3 mM DTT, 270 µM coenzyme A, 470 µM luciferin (Chemie Brunschwig AG), 530 µM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves. In this assay, compounds of the invention inhibit anti-T cell receptor/anti-CD28 and PMA/ionomycin stimulated Jurkat cells with an $IC_{50} \leq 1$ µM.

9. Alloqeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 µg/ml streptomycin (Gibco BRL, Basel, Switzerland), 50 µM 2-mercaptoethanol (Fluka, Buchs, Switzerland) and serially diluted compounds. Seven three-fold dilution steps in duplicates per test compound are performed. After four days of incubation 1 µCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined.

Results

The compounds of the invention may typically exhibit a selectivity of around 10 fold, also typically around 20 fold, and usually around 100 fold for the PKC isoforms α and β, and optionally θ, over one or more of the other PKC isoforms, e.g. over one or more PKC isoforms selected from δ, ε, and η, typically over the PKC isoform δ, also typically over the PKC isoforms ε and η and generally over the PKC isoforms δ, ε and η.

Selectivity for the α, β or θ isoforms of the PKC over one or more of the other PKC isoforms may be determined by comparing the $IC_{50}$ of the compound for the α, β or θ PKC to the $IC_{50}$ of the compound for the other PKC isoforms, e.g. δ, ε, η. Said selectivity may be determined by calculating the ratio of $IC_{50}$ of the compound for the δ, ε or η PKC isoforms to the $IC_{50}$ of the compound for the α, β or θ PKC. $IC_{50}$ values may be obtained, for example, according to the PKC assay described below.

Typically compounds of the invention may exhibit an $IC_{50}$ value for the α and β, and optionally θ, PKCs of $\leq 1$ µM, preferably <100 nM, more preferably $\leq 50$ nM, even more preferably $\leq 25$ nM in the hereinabove mentioned assay.

B. In vivo

Rat Heart Transplantation

The strain combination used: Male Lewis ($RT^1$ haplotype) and BN ($RT^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 10/0 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when heart beat stops. Increases of graft survival are obtained in animals treated with a compound of the invention administered orally at a daily dose of 1 to 30 mg/kg bid.

Graft v. Host Model

Spleen cells ($2 \times 10^7$) from Wistar/F rats are injected subcutaneously into the right hind footpad of (Wistar/F×Fischer 344)$F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound.

The compounds of the invention are, therefore, useful in the treatment and/or prevention of diseases or disorders mediated by T lymphocytes and/or PKC e.g. acute or chronic rejection of organ or tissue allo- or xenografts, graft versus host diseases, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as AIDS, septic shock or adult respiratory distress syndrome, ischemia/reperfusion injury e.g. myocardial infarction, stroke, gut ischemia, renal failure or hemorrhage shock, or traumatic shock, e.g. traumatic brain injury. The compounds of the invention are also useful in the treatment and/or prevention of T-cell mediated acute or chronic inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes type I or II and the disorders associated therewith, respiratory diseases such as asthma or inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis. For the above uses the required dosage will of course vary depending on the mode of administration, the particular condition to be treated and the effect desired. In general, satisfactory results are indicated to be obtained systemically at daily dosages of from about 0.1 to about 100 mg/kg body weight. An indicated daily dosage in the larger mammal, e.g. humans, is in the range from about 0.5 mg to about 2000 mg, conveniently administered, for example, in divided doses up to four times a day or in retard form.

The compounds of the invention are also useful in the treatment and/or prevention of cardiovascular diseases and disorders, e.g. hypertension, cardiovascular ischemia, or for improving cardiac function following ischemia. The compounds of the invention are also useful in the treatment and/or prevention of ocular diseases and disorders, e.g. involving inflammation and neovascularization.

The compounds of the invention may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of the invention in free form or in pharmaceutically acceptable salt form in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

Topical administration is e.g. to the skin. A further form of topical administration is to the eye.

The compounds of the invention may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by T lymphocytes and/or PKC, e.g. such as indicated above, in a subject in need of such treatment, which method comprises administering to said subject an effective amount of a compound of the invention, e.g. a selective inhibitor of PKCs α and β, and optionally θ, or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of the invention, e.g. a selective inhibitor of PKCs α and β, and optionally θ, or a pharmaceutically acceptable salt thereof;

1.3 A method for preventing or treating cardiovascular diseases and disorders, e.g. hypertension, cardiovascular ischemia, or for improving cardiac function following ischemia; in a subject in need of such treatment, which method comprises administering to said subject an effective amount of a compound of the invention, e.g. a selective inhibitor of PKCs α and β, and optionally θ, or a pharmaceutically acceptable salt thereof;

1.4 A method for preventing or treating ocular diseases and disorders, e.g. involving inflammation and neovascularization, e.g. as indicated above, in a subject in need of such treatment, which method comprises administering to said subject an effective amount of a compound of the invention, e.g. a selective inhibitor of PKCs α and β, and optionally θ, or a pharmaceutically acceptable salt thereof;

2. A compound of the invention, e.g. a selective inhibitor of PKCs α and β, and optionally θ, in free form or in a pharmaceutically acceptable salt form for use as a pharmaceutical, e.g. in any of the methods as indicated under 1.1 to 1.4 above.

3. A pharmaceutical composition, e.g. for use in any of the methods as in 1.1 to 1.4 above comprising a compound of the invention, e.g. a selective inhibitor of PKCs α and β, and optionally θ, in free form or pharmaceutically acceptable salt form in association with a pharmaceutically acceptable diluent or carrier therefor.

4. A compound of the invention, e.g. a selective inhibitor of PKCs α and β, and optionally θ, or a pharmaceutically acceptable salt thereof for use in the preparation of a pharmaceutical composition for use in any of the method as in 1.1 to 1.4 above.

Compounds of the invention may be administered as the sole active ingredient or together with other drugs in immunomodulating regimens or other anti-inflammatory agents e.g. for the treatment or prevention of allo- or xenograft acute or chronic rejection or inflammatory or autoimmune disorders. For example, they may be used in combination with cyclosporines, or ascomycines or their immunosuppressive analogs or derivatives, e.g. cyclosporin A, ISA Tx247, FK-506, ABT-281, ASM 981; an mTOR inhibitor, e.g. rapamycin, 40-O-(2-hydroxyethyl)-rapamycin, CC1779, ABT578, or a rapalog, e.g. AP23573, AP23464, AP23675, AP23841, TAFA-93, biolimus 7 or biolimus 9 etc.; corticosteroids; cyclophosphamide; azathioprene; methotrexate; an EDG receptor agonist having accelerating lymphocyte homing properties, e.g. FTY 720 or an analogue thereof; leflunomide or analogs thereof; mizoribine; mycophenolic acid or a salt thereof, e.g. sodium salt; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists. Compounds of the invention may also be administered together with an antiproliferative drug, e.g. a chemotherapeutic drug, e.g. as used in cancer treatment, including but not limited to aromatase inhibitors, antiestrogens, topoisomerase I inhibitors, topoisomerase 11 inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide, or with an anti-diabetic drug, an insulin secretagogue or insulin secretion enhancer, e.g. a sulphonyl urea, e.g. tolbutamide, chlorpropamide, tolazamide, acetohexamide, 4-chloro-N-[(1-pyrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide or tolylcyclamide, an oral insulinotropic agent derivative, e.g. a short acting insulin enhancer, e.g. meglitinide, repaglinide, a phenyl acetic acid derivative, e.g.nateglinide, a DPP IV inhibitor, e.g. 1-{2-[(5-cyanopyridin-2-yl)amino]ethylamino}acetyl-(2S)-cyano-pyrrolidine di-hydrochloride, LAF237, GLP-1 or a GLP-1 agonist analog, or an insulin sensitizer e.g. a peroxisome proliferator activated receptor.γagonist (PPARγ), e.g. a glitazone, a non-glitazone type such as a N-(2-benzoylphenyl)-L-tyrosine analogue, e.g. GI-262570, or an oxolidinedione, e.g. JTT501, a dual PPARγ/PPARα agonist, e.g. DRF-554158, NC-2100 or NN-622, a retinoid X receptor agonist or a rexinoid, e.g. 2-[1-(3,5,5,8,8-pentamethyl-5,6,7,8-tetrahydro-2-naphthyl)-cyclopropyl]-pyridine-5-carboxylic acid, 4-[(3,5,5,8,8-pentamethyl-5,6,7,8-tetrahydro-2-naphthyl)-2-carbonyl]-benzoic acid, 9-cis retinoic acid or an analog, derivative or a pharmaceutically acceptable salt thereof, in diabetes therapy, In accordance with the foregoing the present invention provides in a yet further aspect:

5. A method as defined above comprising co-administration, e.g. concomitantly or in sequence, of a therapeutically effective amount of an inhibitor of PKC or of T-cell activation and proliferation, e.g. a compound of the invention in free form or in pharmaceutically acceptable salt form, and a second drug substance, said second drug substance being an immunosuppressant, immunomodulatory, anti-inflammatory, antiproliferative or anti-diabetic drug, e.g. as indicated above.

6. A therapeutic combination, e.g. a kit, comprising a) an inhibitor of PKC or of T-cell activation and proliferation, e.g. a compound of the invention, in free form or in pharmaceutically acceptable salt form, and b) at least one second agent selected from an immunosuppressant, immunomodulatory, anti-inflammatory, antiproliferative and anti-diabetic drug. Component a) and component b) may be used concomitantly or in sequence. The kit may comprise instructions for its administration.

Where an inhibitor of PKC or of T-cell activation and proliferation, e.g. a compound of the invention, e.g. a selective inhibitor of PKCs α and β, and optionally θ, is administered in conjunction with other immunosuppressive/immunomo-dulatory, anti-inflammatory, antiproliferative or anti-diabetic therapy, e.g. for preventing or treating acute or chronic graft rejection or inflammatory or autoimmune disorders as hereinabove specified, dosages of the co-administered immunosuppressant, immunomodulatory, anti-inflammatory, antiproliferative or anti-diabetic compound will of course vary depending on the type of co-drug employed, e.g. whether it is a steroid or a cyclosporine, on the specific drug employed, on the condition being treated and so forth.

Compounds of the invention, i.e. of formula (1), have an interesting pharmacokinetic profile and interesting in vitro and in vivo activities.

The invention claimed is:

1. A compound of formula (I)

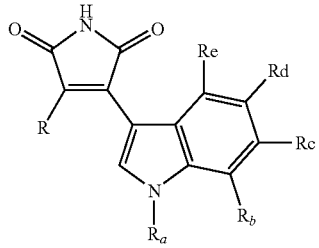

(I)

wherein $R_a$ is hydrogen or $C_{1-6}$alkyl optionally substituted by OH, halogen, $NH_2$, $NHC_{1-6}$alkyl, $N(C_{1-6}$alkyl$)_2$, $C_{1-6}$alkoxy, $C_{3-8}$cycloalkyl or heterocyclic residue;

$R_b$ is hydrogen; halogen; CN; $C_{1-6}$alkyl optionally substituted with OH, halogen, $C_{1-6}$alkoxy, $NH_2$, $NHC_{1-6}$alkyl, or $N(C_{1-6}$alkyl$)_2$; optionally substituted $C_{1-6}$alkoxy; or optionally substituted $C_{1-6}$alkoxy-chain; wherein said $C_{1-6}$alkoxy and said $C_{1-6}$alkoxy-chain are optionally substituted with OH, halogen, $NH_2$, $NHC_{1-6}$alkyl, $N(C_{1-6}$ alkyl$)_2$, $C_{1-6}$alkoxy, $C_{3-8}$cycloalkyl or heterocyclic residue;

$R_c$ is hydrogen; halogen; CN; optionally substituted $C_{1-6}$alkyl; optionally substituted $C_{1-6}$alkoxy; wherein $C_{1-6}$alkyl and $C_{1-6}$alkoxy are optionally substituted with OH, halogen, $NH_2$, $NHC_{1-6}$alkyl, $N(C_{1-6}$alkyl$)_2$, $C_{1-6}$alkoxy, $C_{3-8}$cycloalkyl or heterocyclic residue;

each of $R_d$ and $R_e$ independently, is hydrogen; halogen; CN; optionally substituted $C_{1-6}$alkyl; wherein $C_{1-6}$alkyl is optionally substituted with OH, halogen, $NH_2$, $NHC_{1-6}$ alkyl, $N(C_{1-6}$alkyl$)_2$, $C_{1-6}$alkoxy, $C_{3-8}$cycloalkyl or heterocyclic residue;

wherein R is a radical of formula (a), (b), (c), (d), or (f):

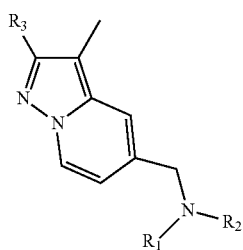

(a)

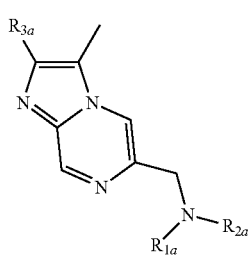

(b)

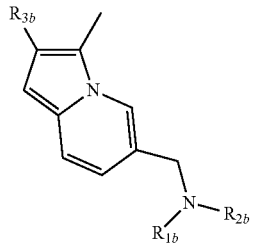

(c)

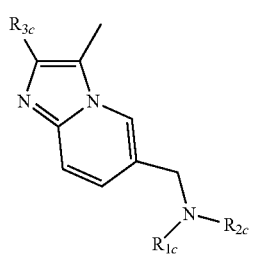

(d)

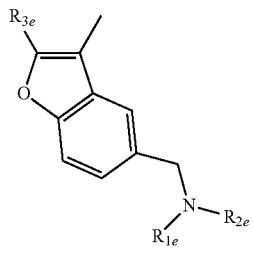

(f)

wherein either each of $R_1$, $R_{1a}$, $R_{1b}$, $R_{1c}$, $R_{1d}$, $R_{1e}$, $R_2$, $R_{2a}$, $R_{2b}$, $R_{2c}$, $R_{2d}$, and $R_{2e}$ independently, is hydrogen; $C_{1-6}$alkyl optionally interrupted by an oxygen atom and optionally substituted by OH, $C_{1-6}$alkoxy, $NH_2$, $NHC_{1-4}$alkyl, $N(C_{1-4}$alkyl$)_2$, $C_{3-8}$cycloalkyl or heterocyclic residue; $C_{3-8}$cycloalkyl; or halo$C_{1-6}$alkyl;

or $R_1$ and $R_2$, $R_{1a}$ and $R_{2a}$, $R_{1b}$ and $R_{2b}$, $R_{1c}$ and $R_{2c}$, $R_{1d}$ and $R_{2d}$, or $R_{1e}$ and $R_{2e}$, respectively, form together with the nitrogen atom to which they are bound a heterocyclic residue;

each of $R_3$, $R_{3a}$, $R_{3b}$, $R_{3c}$, $R_{3d}$, and $R_{3e}$ independently, is hydrogen; halogen; CN; $NO_2$; $C_{1-6}$alkyl; halo$C_{1-6}$alkyl;

R' is hydrogen; $C_{1-6}$alkyl; halo-$C_{1-6}$alkyl; $CH_2$-$C_{1-5}$alkyl, the $C_{1-5}$alkyl being optionally substituted by OH, $C_{1-6}$alkoxy, $NH_2$, $NHC_{1-6}$alkyl, or $N(C_{1-6}$alkyl$)_2$;

or a pharmaceutically acceptable salt thereof.

2. The compound of claim 1, wherein $R_a$ is hydrogen or $C_{1-6}$alkyl.

3. The compound of claim 1, wherein $R_b$ is hydrogen; $C_{1-6}$alkyl; halo-$C_{1-6}$alkyl; $C_{1-6}$alkoxy unsubstituted or substituted by halogen; $C_{1-6}$alkoxy-chain unsubstituted or substituted by halogen.

4. The compound of claim 1, wherein $R_b$ is hydrogen or methyl.

5. The compound of claim 1, wherein $R_c$ is hydrogen or $C_{1-6}$alkyl.

6. The compound of claim 1, wherein $R_d$ is hydrogen or $C_{1-6}$alkyl.

7. A pharmaceutical composition comprising a compound in accordance to claim 1 or a pharmaceutically acceptable salt thereof and a pharmaceutically acceptable diluent or carrier therefore.

* * * * *